United States Patent
Chodavarapu et al.

(10) Patent No.: US 11,406,598 B2
(45) Date of Patent: Aug. 9, 2022

(54) LYOPHILIZED COMPOSITIONS OF PHENOBARBITAL SODIUM SALT

(71) Applicant: Nivagen Pharmaceuticals, Inc., Sacramento, CA (US)

(72) Inventors: Bala Tripura Sundari Chodavarapu, Davis, CA (US); Thirupathi Mangali, Sacramento, CA (US); Jay Shukla, Sacramento, CA (US); Anand Shukla, Denver, CO (US); Dasaradhi Lakkaraju, Sacramento, CA (US)

(73) Assignee: NIVAGEN PHARMACEUTICALS, INC., Sacramento, CA (US)

( * ) Notice: Subject to any disclaimer, the term of this patent is extended or adjusted under 35 U.S.C. 154(b) by 0 days.

(21) Appl. No.: 17/025,881

(22) Filed: Sep. 18, 2020

(65) Prior Publication Data

US 2021/0085608 A1    Mar. 25, 2021

Related U.S. Application Data

(60) Provisional application No. 62/903,511, filed on Sep. 20, 2019.

(51) Int. Cl.
  *A61K 9/19*  (2006.01)
  *A61K 31/515*  (2006.01)
  *A61K 9/00*  (2006.01)

(52) U.S. Cl.
  CPC .............. *A61K 9/19* (2013.01); *A61K 9/0019* (2013.01); *A61K 31/515* (2013.01)

(58) Field of Classification Search
  CPC ....... A61K 9/19; A61K 9/0019; A61K 31/515
  See application file for complete search history.

(56) References Cited

U.S. PATENT DOCUMENTS

| 6,077,545 | A | * | 6/2000 | Roskos | A61K 9/0019 424/649 |
| 8,436,190 | B2 | † | 5/2013 | Brittain | |
| 2010/0035904 | A1 | * | 2/2010 | Sun | A61P 25/20 514/270 |
| 2017/0143719 | A1 | * | 5/2017 | Parker | A61K 31/515 |

FOREIGN PATENT DOCUMENTS

| CN | 104940149 A | 9/2015 |
| WO | 2017085687 A1 | 5/2017 |

OTHER PUBLICATIONS

Staudt, title: Phenobarbital in newborn infants: Overview, Monatsschr Kinderheilkd; vol. 132, issue 4, pp. 194-202; Apr. 1984 (Year: 1984).*

(Continued)

*Primary Examiner* — Carlos A Azpuru
(74) *Attorney, Agent, or Firm* — Umberg Zipser LLP

(57) ABSTRACT

A composition of, method for producing, and use of an amorphous lyophilized Phenobarbital Sodium having high purity are presented. The amorphous lyophilized Phenobarbital Sodium is storage-stable being essentially void of impurities (e.g., phenylethylacetylurea (PEAU), 2-ethyl-2-phenylmalonamide (2EPMM), and/or alpha-phenylbutyrylguanidine (PBG)) upon reconstitution in water.

15 Claims, 39 Drawing Sheets

(56) References Cited

OTHER PUBLICATIONS

Kelly et al, title: phenobarbital sodium, Critical Care Trauma Centre, last update: Oct. 11, 2018. (Year: 2018).*
Dietz et al, title: Phenobarbital Stability in different dosage forms: alternatives for Elixirs, Pharmaceutical Research, vol. 5, No. 12; pp. 803-805, 1988 (Year: 1988).*
Snyder, title: Lyophilization: the Basics; Drug discovery and development, pp. 1-5, Mar. 7, 2017 (Year: 2017).*
Nahata et al, title: Stability of phenobarbital sodium diluted in 0.9% sodium chloride injection; Am J Hosp Pharm, Feb. 1986; vol. 43(2), pp. 384-385; abstract only) (Year: 1986).*
Jatul, title: The stability of solutions of phenobarbital sodium; A dissertation presented to the graduate council of the University of Florid, Feb. 1943 (Year: 1943).*
Nahata et al, title: Stability of phenobarbital sodium diluted in 0.9% sodium chloride injection; Am J Hosp Pharm, Feb. 1986; vol. 43(2), pp. 384-385; full article) (Year: 1986).*
Bardat et al; title: Moisture Measurement: A New Method for Monitoring Freeze-drying Cycles; Technology I Applications; vol. 47, No. 6 / Nov.-Dec. 1993; pp. 293-299. (Year: 1993).*
FDA documnet: Guide to Inspections of Lyophilization of Parenterals, title: Lyophilization of Parenteral; published Nov. 11, 2014. (Year: 2014).*
Gupta, V. Das, "Effect of Ethanol, Glycerol, and Propylene Glycol on the Stability of Phenobarbital Sodium," Journal of Pharmaceutical Sciences, Nov. 1, 1984; 73(11):1661-1662. Abstract only.
Nayyar et al., "Phenytoin-Folate Interactions: How Far is Safe Folate Supplementation in Phenytoin Treated Epileptic Patients?" Journal of Applied Pharmaceutical Science, 2012; 02(06):230-235. Access to Ohio State Dissertations and Theses, https://gradsch.osu.edu/access-distribution (accessed on Jul. 14, 2021).†
Lyophilization of Parenteral (Jul. 1993) (LoP) (https://www.fda.gov/inspections-compliance-enforcement-and-criminal-investigations/inspection-guides/lyophilization-parenteral-793) (dated Nov. 11, 2014) (accessed on Jul. 19, 2021).†
D.S. Przic, et al., Lyophilization—the Process and Industrial Scale, Chem. Ind. vol. 58, No. 12, pp. 552-562, 2004.†
OhioLINK: Frequently Asked Questions, https://etd.ohiolink.edu/apexprod/-f?p=1501:2:310637464866699 (accessed on Jul. 14, 2021).†
Entry from OhioLINK database for Kern, https://etd.ohiolink.edu/apexprod/-rws_olink/r/1501/10?clear=10&p10_accession_num=osu1486476025025146 (accessed on Jul. 14, 2021).†
I.B. Butler, et al., Removal of dissolved oxygen from water: a comparison of four common techniques, Taianta, vol. 41, No. 2, pp. 211-215, 1994.†
R. Sandhyarani, Development and Evaluation of Lyophilized Product of Apo-Acetozolamide, IOSR Journal of Pharmacy; vol. 6, Issue 9 Version. 1, pp. 48-63, Sep. 2016.†
Encyclopedia of Pharmaceutical Technology (2007), vol. 1, Third Edition; James Swarbrick; Freeze, Freeze Drying, Scale-Up Considerations (p. 1807-1874).†
K. Kawada, Phenobarbital sodium lyophilized formulation: Overview of the clinical trial leading to approval of NOBELBAR and package insert information, Neonatal Care, vol. 22, No. 7, pp. 657-663, 2009.†
R.S. Fisher et al., A practical clinical definition of epilepsy, Epilepsia, vol. 55, No. 4, pp. 475-482, 2014.†
K. Kawada et al., A clinical Trial Assessing the Efficacy and Safety of a New Injectable Formula of Sodium Phenobarbital Containing No Additives for the Treatment of Neonatal Seizures, Jpn. J. Clin. Phamacol. Ther., vol. 42, No. 6, pp. 205-210, Jul. 2011.†
O. Bertaux et al., Modification of hepatic alpha-1-glycoprotein and albumin gene expression in rats treated with phenobarbital, Eur. J. Biochem., vol. 203, pp. 655-661, 1992.†
J. Bernstein, Polymorphism in Molecular Crystals, Oxford University Press, Oxford, GB, 2002, ISBN 978-0-19-923656-5.†
Japan Evaluation and Licensing Division, Pharmaceutical and Food Safety Bureau, Deliberation Results Report for Nobelbar for intravenous injection 250 mg, 43 pages, Sep. 16, 2008.†
H. G. Brittain, Polymorphisms in Pharmaceutical Solids, Marcel Dekker, Inc., New York, NY, 1999, ISBN 0-8247-0237-9.†
T. Fournier et al., Phenobarbital Induction of α1-Acid Glycoprotein in Primary Rat Hepatocyte Cultures, Hepatology, vol. 20, No. 6, pp. 1584-1588, 1994.†
J.H. Kern, Freeze Drying as a Method of Processing Some Pharmaceutical Products, Doctor of Philosophy Thesis, the Ohio State University, 1954.†
Nobelpharma Co., Ltd., NOBELBAR 250 mg for Injection, version 12, Nov. 2020.†

\* cited by examiner
† cited by third party

| | Peak Name | RT | Area | Amount | USP Resolution | USP Plate Count | USP Tailing | Assay |
|---|---|---|---|---|---|---|---|---|
| 1 | Phenobarbital | 10.130 | 2396458 | 60.823 | 17.9 | 17534.1 | 1.0 | 112.1 |

| | Peak Name | RT | Area | % Area | Amount | Units | Assay | USP Resolution | USP Tailing |
|---|---|---|---|---|---|---|---|---|---|
| 1 | Benzyl Alcohol | 3.392 | 84435 | 11.25 | 14.537 | mg/mL | 102.0 | 23.7 | 1.7 |
| 2 | Blank | 1.357 | 798 | 0.11 | 0.065 | mg/mL | | | 1.1 |
| 3 | Phenobarbital | 4.536 | 627538 | 83.64 | 51.486 | mg/mL | 86.7 | 7.2 | 1.5 |
| 4 | RRT_1.82 | 8.321 | 37484 | 5.00 | 3.075 | mg/mL | | 14.6 | 1.2 |

| | Peak Name | RT | Area | % Area | Amount | Units | USP Resolution | USP Tailing |
|---|---|---|---|---|---|---|---|---|
| 1 | Benzyl Alcohol | 3.391 | 3972837 | 21.25 | 16.272 | mg/mL | 13.8 | 1.7 |
| 2 | Phenobarbital | 4.537 | 14515521 | 77.64 | 56.435 | mg/mL | 7.1 | 1.5 |
| 3 | RRT_1.82 | 8.321 | 200110 | 1.07 | 0.778 | mg/mL | 14.6 | 1.3 |

| | Peak Name | RT | Area | % Area | Amount | Units | USP Resolution | USP Tailing |
|---|---|---|---|---|---|---|---|---|
| 1 | Benzyl Alcohol | 3.392 | 3833550 | 21.50 | 15.701 | mg/mL | 12.8 | 1.7 |
| 2 | Phenobarbital | 4.536 | 13183528 | 73.94 | 51.257 | mg/mL | 7.1 | 1.5 |
| 3 | RRT_1.82 | 8.321 | 762556 | 4.28 | 2.965 | mg/mL | 14.6 | 1.3 |
| 4 | RRT_1.949 | 9.000 | 42716 | 0.24 | 0.166 | mg/mL | 1.9 | 1.3 |

| Peak Name | RT | Area | Amount | USP Resolution | USP Plate Count | USP Tailing | Assay |
|---|---|---|---|---|---|---|---|
| 1 Phenobarbital | 10.131 | 2358542 | 119.721 | 17.9 | 17563.1 | 1.0 | 110.3 |

| | Peak Name | RT | Area | % Area | Amount | Units | Assay | USP Resolution | USP Tailing |
|---|---|---|---|---|---|---|---|---|---|
| 1 | Benzyl Alcohol | 3.391 | 43440 | 5.94 | 14.958 | mg/mL | 105.0 | | 1.7 |
| 2 | Phenobarbital | 4.537 | 657548 | 89.99 | 107.895 | mg/mL | 90.9 | 7.2 | 1.5 |
| 3 | RRT_1.82 | 8.323 | 29742 | 4.07 | 4.880 | mg/mL | | 14.6 | 1.2 |

| | Peak Name | RT | Area | % Area | Amount | Units | USP Resolution | USP Tailing |
|---|---|---|---|---|---|---|---|---|
| 1 | Benzyl Alcohol | 3.391 | 1984788 | 12.10 | 16.258 | mg/mL | 12.8 | 1.7 |
| 2 | Phenobarbital | 4.536 | 13768702 | 83.93 | 107.064 | mg/mL | 7.1 | 1.5 |
| 3 | RRT_1.82 | 8.322 | 594916 | 3.63 | 4.626 | mg/mL | 14.6 | 1.2 |
| 4 | RRT_1.949 | 8.984 | 48228 | 0.29 | 0.375 | mg/mL | 1.8 | 1.3 |

| Peak Name | RT | Area | Amount | Units | Assay | USP Resolution | s/n | USP Plate Count | USP Tailing |
|---|---|---|---|---|---|---|---|---|---|
| 1 | Phenobarbital | 4.564 | 905459 | 118.985 | mg/mL | 100.2 | 20.7 | 58582 | 8639.9 | 1.1 |
| 2 | Sodium/Blank | 1.133 | 4686 | 8.618 | mg/mL | | | 358.4 | 1316.2 | 1.4 |

LYOPHILIZED COMPOSITIONS OF PHENOBARBITAL SODIUM SALT

RELATED APPLICATIONS

This application claims the benefit of U.S. Provisional Patent Application No. 62/903,511, filed on Sep. 20, 2019, which is incorporated by reference in its entirety.

FIELD OF THE INVENTION

The present disclosure relates to compositions of storage-stable lyophilized Phenobarbital Sodium having high purity that are essentially void of impurities upon reconstitution in water.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Phenobarbital Sodium is a well-known barbiturate that is most commonly administered as an anti-convulsant for the treatment of seizures and may also be administered as a sedative, a sleep aide, or a pre-anesthetic. Phenobarbital Sodium is typically a liquid formulation administered intramuscularly (IM) or intravenously (IV) with crystalline granules or crystals dissolved in an aqueous solvent. For example, WO 2017/085687 to Parker et al. discloses a liquid formulation of Phenobarbital Sodium dissolved in water along with a C1-C4 alcohol and a glycol.

The stability of solubilized Phenobarbital Sodium has been a recurring problem because it readily hydrolyzes in water forming various degradation products. In particular, in water alone or in water with an increase in pH, Phenobarbital Sodium forms the degradation products phenylethylacetylurea (PEAU), 2-ethyl-2-phenylmalonamide (2EPMM), and alpha-phenylbutyrylguanidine (PBG). While these degradation impurities may not directly compromise the effectiveness of the Phenobarbital Sodium for its therapeutic activity, these degradation impurities are toxic and cause severe side effects. Specifically, PEAU was previously administered as Pheneturide for severely affected epileptics. However, the Food and Drug Administration (FDA) withdrew approval of Pheneturide due to its toxic effects. In particular, Pheneturide is reported to be a potent liver enzyme inducer that disrupts both calcium and folate metabolism. (Nayyar et al., 2012, *J. of Appl. Pharm Sci.*, 2:230-235.) Prior to its removal as an FDA-approved drug, patients treated with Pheneturide showed low levels of serum calcium and folate.

Over the years of medical administration, efforts have been made to decrease the formation of the toxic degradation products in the Phenobarbital Sodium liquid formulation. For example, Gupta, V. D., (*J. Pharm Sci.*, 1984, 73:1661-1662) describes the effects of ethanol, glycerol, and propylene glycol on the stability of Phenobarbital Sodium in aqueous solutions. Specifically, Gupta discloses that ethanol has the best effect followed by propylene glycol and glycerol relative to water alone. Years after Gupta, Parker et al., (WO 2017/085687) focused on minimizing the total amount of water to reduce the hydrolysis and consequently the formation of the degradation products. Parker addresses the hydrolysis issue by limiting the amount of water (e.g., to no more than 50 mg/mL) in the liquid formulation. Parker's minimized water formulations also include a C1-C4 alcohol such as ethanol and a glycol such as propylene glycol. However, while the amount of impurities in Parker's liquid formulation may have decreased compared to prior formulations, impurities such a PEAU are still present in undesirable amounts, particularly after extended storage.

In addition to the degradation impurities, the current marketed liquid formulation of Phenobarbital Sodium (e.g., Phenobarbital Sodium for Injection USP, 65 mg/mL or 130 mg/mL), includes organic solvents such as alcohol, which are not desirable in general and indeed not suitable for administration to newborns as described in the art, e.g., Williams et al., 1998, "Evaluating Toxic Alcohol Poisoning in the Emergency Setting," *Laboratory Medicine*, Vol. 29, No. 2; Wood et al., 2007, *J. of Perinatology*, 27:183-185; Kumar, 1985, "Adverse Drug Reactions in the Newborn," *Annals of Clin. And Lab. Sci*, Vol. 15, No. 3; and Cuzzolin, 2018, *J. Pediatric and Neonatal Individualized Med.*, doi: 10.7363/070112.

Accordingly, there is still a need for a stable Phenobarbital Sodium formulation in a formulation that is storage stable and void or essentially void of degradation impurities upon solubilization in water.

SUMMARY

Disclosed herein are compositions of, methods of producing, and use of a lyophilized Phenobarbital Sodium formulation. The contemplated composition is an amorphous lyophilized Phenobarbital Sodium with high stability and purity. The lyophilized composition may include no less than 98% Phenobarbital Sodium. The amorphous composition is a storage-stable form of lyophilized Phenobarbital Sodium.

The lyophilized amorphous formulation that was produced resulted in surprising, unexpected and desirable results. The quantity of undesirable and/or toxic degradation impurities that are produced from this formulation are less than those in current commercial products. And the stability of this formulation is superior to that of current commercial products. These results are particularly surprising and unexpected in view of the fact that conventional wisdom teaches that crystalline material is more stable than amorphous material (see e.g., C. Ahlneck and G. Zografi "The Molecular Basis for Moisture Effects on the Physical and Chemical Stability of Drugs in the Solid-State," Int. J. Pharm. 1990, 62, 87-95). Thus, one of ordinary skill in the art would want to avoid using amorphous material in pharmaceutical formulations.

Preferably the percentage of the lyophilized formulation that is amorphous is at least 20%, 25%, 30%, 35%, 40%, 45%, 50%, 55%, 60%, 65%, 70%, 75%, 80%, 85%, 90%, or 95%. Alternatively, the percentage of the lyophilized formulation that is amorphous can be 100%. In addition, the percentage of the lyophilized formulation that is amorphous can be within any range between (and including) 20% to 100% (e.g., 20%-100%, 25%-95%. etc.).

Methods for producing the storage-stable form of lyophilized Phenobarbital Sodium composition result in a lyophilized powder in which the impurity phenylethylacetylurea (PEAU) is below detection limit and is never more than 0.2% of the specification limit even after storage of the lyophilized Phenobarbital Sodium for up to 6 months under accelerated stability conditions (40° C., 75% RH). In some embodiments, the method for producing the storage-stable lyophilized Phenobarbital Sodium includes adding Phenobarbital Sodium to water to form a Phenobarbital Sodium solution, having a pH between 9.2 to 10.2, and lyophilizing the bulk solution. In some embodiments, the water is Water for Injection.

In preferred embodiments, the Water for Injection is sparged with nitrogen prior to adding the Phenobarbital Sodium. Typically, the Water for Injection is sparged with nitrogen for at least 30 minutes prior to adding the Phenobarbital Sodium. In additional embodiments, the water (e.g., Water for Injection) is cooled to or between 2 to 8° C. prior to adding the Phenobarbital Sodium.

For adjusting the pH of the Phenobarbital Sodium solution, the method for producing the storage-stable form of lyophilized Phenobarbital Sodium composition may also include measuring the pH of the Phenobarbital Sodium solution, wherein if the pH is higher than 10.2, the adjusting includes adding hydrochloric acid (HCl).

Typically, the resulting lyophilized Phenobarbital Sodium forms no more than 0.1% PEAU when reconstituted in an aqueous solution after storage of the lyophilized Phenobarbital Sodium for up to 6 months both at RT and accelerated stability conditions. More typically, the resulting lyophilized Phenobarbital Sodium forms no more than 0.05% PEAU when reconstituted in an aqueous solution after storage of the lyophilized Phenobarbital Sodium for up to 6 months at room temperature (RT) and under accelerated stability conditions (40° C.). Additionally, or alternatively, the resulting lyophilized Phenobarbital Sodium forms either an amount below the quantitative limit (BQL, 0.05%) or no detectable amount of PEAU, 2-ethyl-2-phenylmalonamide (2EPMM), or alpha-phenylbutyrylguanidine (PBG) when reconstituted in the aqueous solution after storage of the lyophilized Phenobarbital Sodium for up to 6 months at RT and accelerated stability conditions.

According to contemplated embodiments as disclosed herein, the amorphous lyophilized Phenobarbital Sodium composition is stable up to at least 6 months under accelerated stability conditions which is equivalent to 24 months at RT. In this respect, in some embodiments, the stability of the lyophilized Phenobarbital Sodium is determined by reconstituting the lyophilized Phenobarbital Sodium in an aqueous solution and measuring the amount of or the presence of phenylethylacetylurea (PEAU), 2-ethyl-2-phenylmalonamide (2EPMM), and/or alpha-phenylbutyrylguanidine (PBG).

Additional embodiments include the method for producing the storage-stable form of lyophilized Phenobarbital Sodium composition as disclosed in which the Phenobarbital Sodium solution is filtered prior to lyophilization.

Further embodiments include the method for producing the storage-stable form of lyophilized Phenobarbital Sodium composition as disclosed in which the Phenobarbital Sodium solution is aliquoted into a vial prior to lyophilization, and after lyophilization, a closure is applied to the vial under vacuum.

Aspects of the present disclosure also include a method of reducing formation of degradation products of Phenobarbital Sodium reconstituted in an aqueous solution, in which the method includes adding Phenobarbital Sodium to water to form a Phenobarbital Sodium solution, adjusting the pH of the Phenobarbital Sodium solution to or between 9.2 to 10.2, and lyophilizing the Phenobarbital Sodium solution to form stable white lyophilized powder of Phenobarbital Sodium.

In preferred embodiments, the Water for Injection is sparged with nitrogen prior to adding the Phenobarbital Sodium. Typically, the Water for Injection is sparged with nitrogen for at least 30 minutes prior to adding the Phenobarbital Sodium. In additional embodiments, the water (e.g., Water for Injection) is cooled to or between 2 to 8° C. prior to adding the Phenobarbital Sodium.

For adjusting the pH of the Phenobarbital Sodium solution, the method of reducing formation of degradation products of Phenobarbital Sodium reconstituted in an aqueous solution may also include measuring the pH of the Phenobarbital Sodium solution, wherein if the pH is higher than 10.2, the adjusting includes adding Hydrochloric acid (HCl).

In typical embodiments, the degradation products of Phenobarbital Sodium reconstituted in an aqueous solution include phenylethylacetylurea (PEAU), 2-ethyl-2-phenylmalonamide (2EPMM), and/or alpha-phenylbutyrylguanidine (PBG), and analysis of the formation of the degradation products includes reconstituting the stable lyophilized Phenobarbital Sodium in an aqueous solution to form a reconstituted solution, and quantitating the amount of or presence of PEAU, 2 EPMM, and/or PBG in the reconstituted solution.

In typical embodiments, the method of reducing formation of degradation products of Phenobarbital Sodium reconstituted in an aqueous solution results in the reconstituted solution having no less than 96% Phenobarbital Sodium. In more typical embodiments, the reconstituted solution has no less than 97% Phenobarbital Sodium. In some preferred embodiments, the reconstituted solution has no less than 98% Phenobarbital Sodium, and in other preferred embodiments between 95% and 105% Phenobarbital Sodium. In additional or alternative embodiments, the reconstituted solution has no more than 0.2% PEAU, 2 EPMM, and/or PBG, and preferably has 0.05% or less PEAU and no detectable amount of 2 EPMM or PBG.

Further aspects of the present disclosure include methods of treating an individual in need of Phenobarbital Sodium. These methods include adding saline or dextrose to the lyophilized powder of Phenobarbital Sodium as disclosed herein immediately prior to administration to form a Phenobarbital Sodium reconstituted solution and administering the Phenobarbital Sodium reconstituted solution to the individual. In some embodiments, the individual in need of Phenobarbital Sodium suffers from epilepsy. In particular embodiments, the individual in need of Phenobarbital Sodium is a newborn suffering from neonatal epilepsy. In other embodiments, the lyophilized amorphous Phenobarbital Sodium is a powder dose of 65 mg, 130 mg, 100 mg or 200 mg. In typical embodiments, the administering of the Phenobarbital Sodium reconstituted solution to the individual includes intramuscular injection or intravenous injection.

Additional aspects of the present disclosure include a pharmaceutical product including a vial containing the white lyophilized powder of Phenobarbital Sodium for reconstitution prior to administration, in which the composition was lyophilized in the vial and the vial includes a closure positioned in order to seal the vial under vacuum after Lyophilization.

Therefore, the inventors also contemplate lyophilized Phenobarbital Sodium.

Various objects, features, aspects, and advantages will become more apparent from the following detailed description of preferred embodiments, along with the accompanying drawings.

DETAILED DESCRIPTION

The inventors have surprisingly discovered a method for making a storage-stable and highly purified Phenobarbital Sodium composition that is void of any detectable impurities in its lyophilized powder form and is essentially void of impurities upon reconstitution in water. The contemplated Phenobarbital Sodium composition is a lyophilized powder that is no less than 98% Phenobarbital Sodium and is stable (25° C., 65% RH and 40° C., 75% RH) for up to at least 6 months under accelerated conditions which is equivalent to 24 months at RT. Upon reconstitution (e.g. solubilization/resuspension) in water, the lyophilized Phenobarbital Sodium forms no more than 0.05% of 2-ethyl-2-phenylmalonamide (2EPMM) or alpha-phenylbutyrylguanidine (PBG), and phenylethylacetylurea (PEAU).

The Phenobarbital Sodium composition as described herein refers to Phenobarbital Sodium having an IUPAC (International Union of Pure and Applied Chemistry) name of sodium 5-ethyl-4,6-dioxo-5-phenyl-1H-pyrimidin-2-olate, a Chemical Abstract Service (CAS) No. 57-30-7, and a molecular formula of $C_{12}H_{11}N_2NaO_3$.

In order to avoid hydrolysis of Phenobarbital Sodium and therefore the formation of its toxic degradation products, the inventors have unexpectedly discovered that a lyophilized Phenobarbital Sodium formed by the methods disclosed herein results in a storage-stable lyophilized powder of Phenobarbital Sodium. In particular, with reference to the polarized light photomicrographs of FIGS. 1A-1F and the XRPD analysis shown in FIG. 5A-5D, the storage-stable lyophilized powder of Phenobarbital Sodium has an amorphous structure. Without wishing to be bound by any theory or hypothesis, the lyophilized Phenobarbital Sodium produced following the methods according to embodiments of the present disclosure produces an amorphous structure that contributes to the observed stability of this composition upon reconstitution in water. Irrespective of the mechanism of action, the contemplated lyophilized Phenobarbital Sodium composition is stable and upon reconstitution in water, does not form significant (e.g., not measurable or not detectable) amounts of the toxic degradation products—namely PEAU, 2EPMM, or PBG.

Figure 1A:
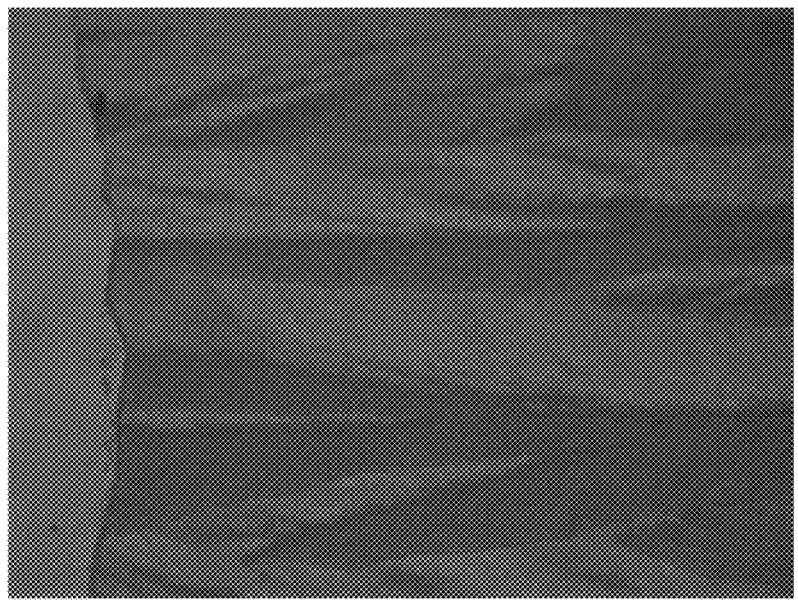
FIG. 1A is a polarized light photomicrograph of the presently disclosed Phenobarbital Sodium in water during Lyophilization microscopy at −50° C., as indicated.
Figure 1B:
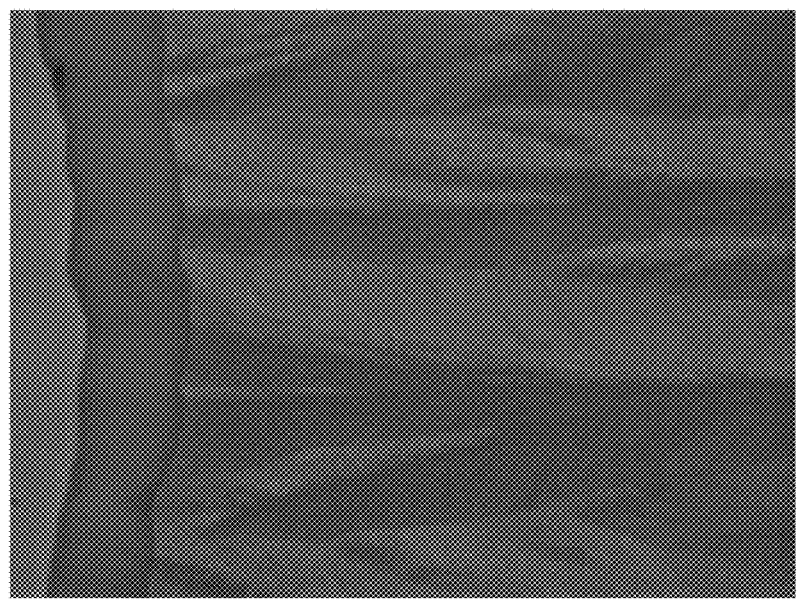
FIG. 1B is a polarized light photomicrograph of the presently disclosed Phenobarbital Sodium in water during Lyophilization microscopy at −45.5° C. as indicated.
Figure 1C:
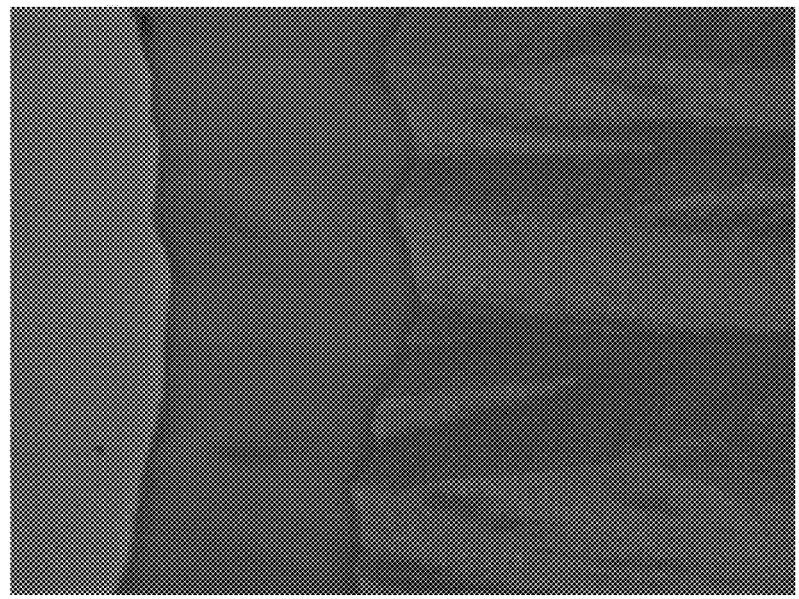
FIG. 1C is a polarized light photomicrograph of the presently disclosed Phenobarbital Sodium in water during Lyophilization microscopy at −40.0° C. as indicated.
Figure 1D:
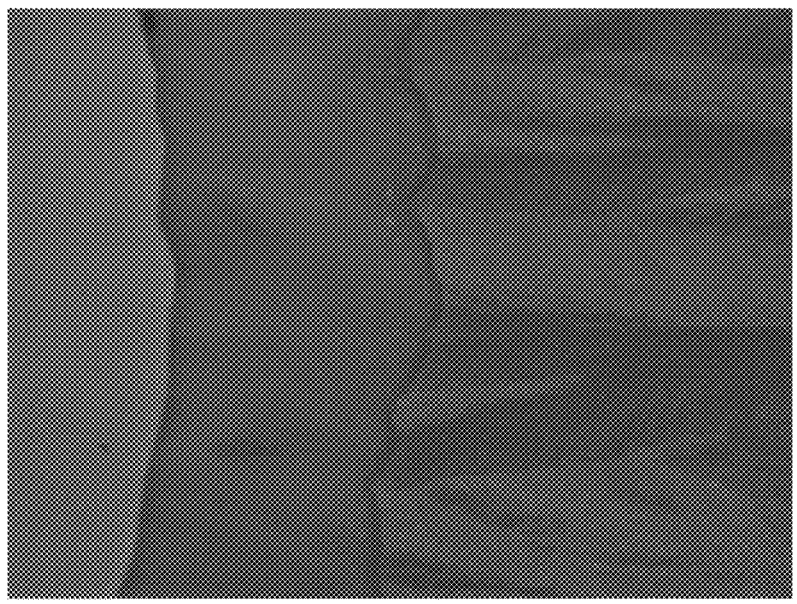
FIG. 1D is a polarized light photomicrograph of the presently disclosed Phenobarbital Sodium in water during Lyophilization microscopy at −39.6° C. as indicated.
Figure 1E:
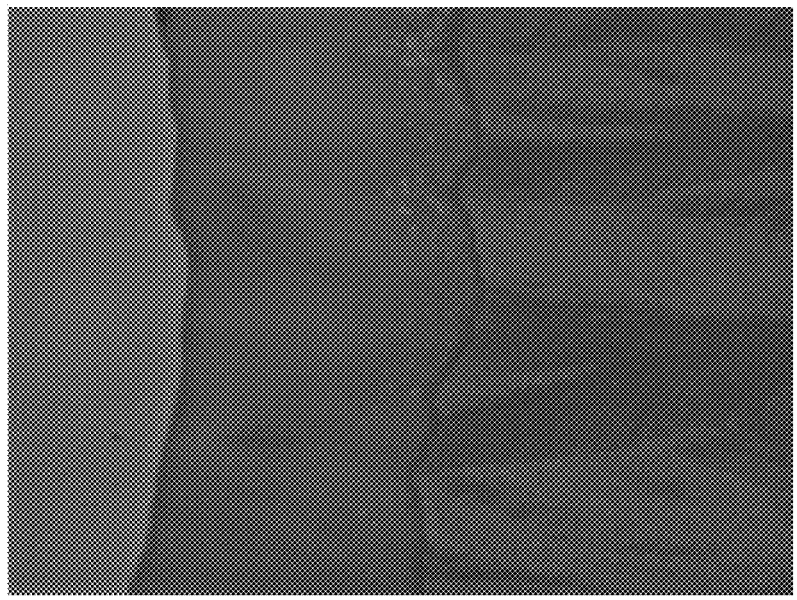
FIG. 1E is a polarized light photomicrograph of the presently disclosed Phenobarbital Sodium in water during Lyophilization microscopy at −39.2° C. as indicated.
Figure 1F:
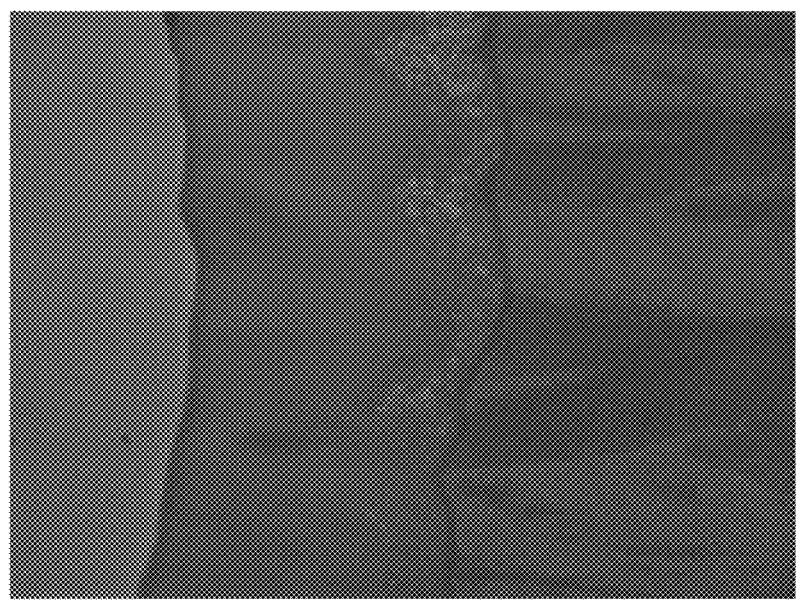
FIG. 1F is a polarized light photomicrograph of the presently disclosed Phenobarbital Sodium in water during Lyophilization microscopy at −38.8° C. as indicated.
Figure 2A:
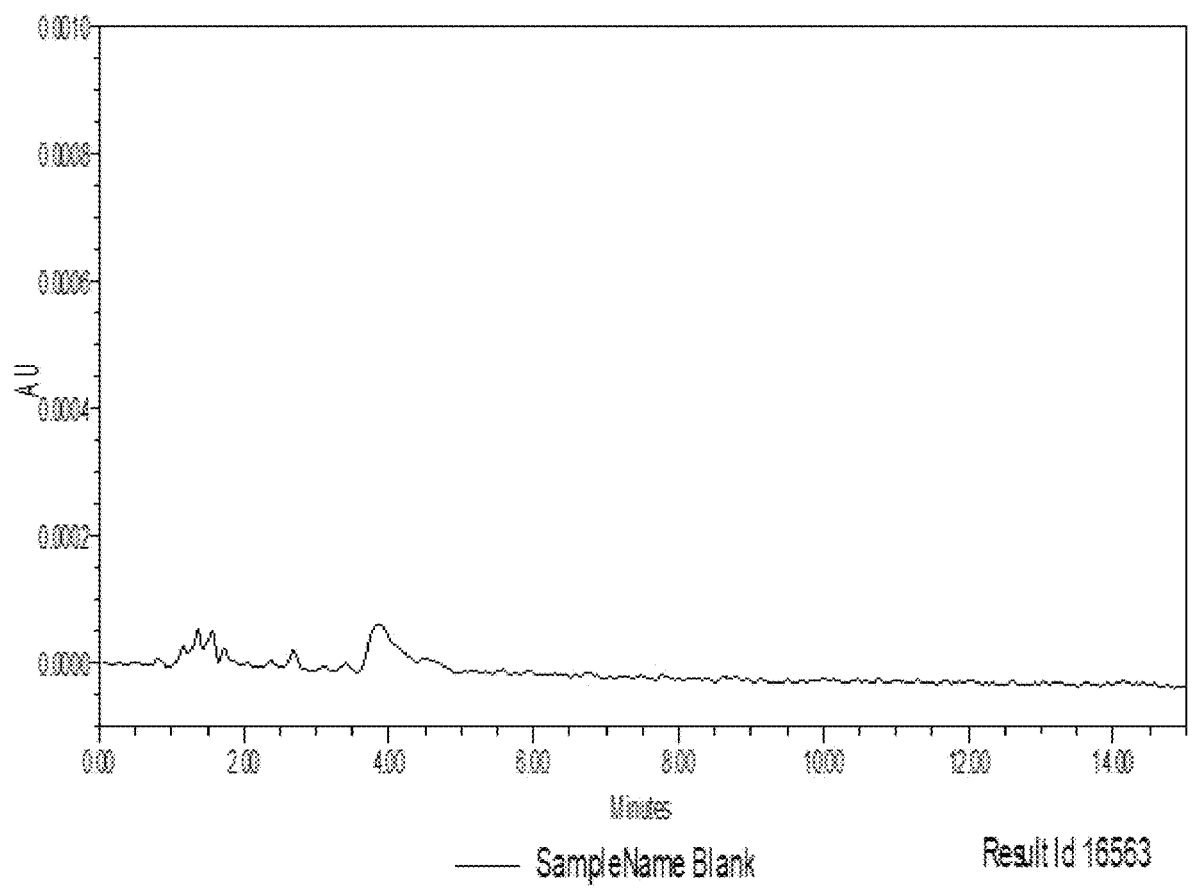
FIG. 2A is a chromatogram from an injection of a "blank solution" for assay by high performance liquid chromatography (HPLC) at a detection wavelength of 210 nanometers (nm), as described herein.
Figure 2B:
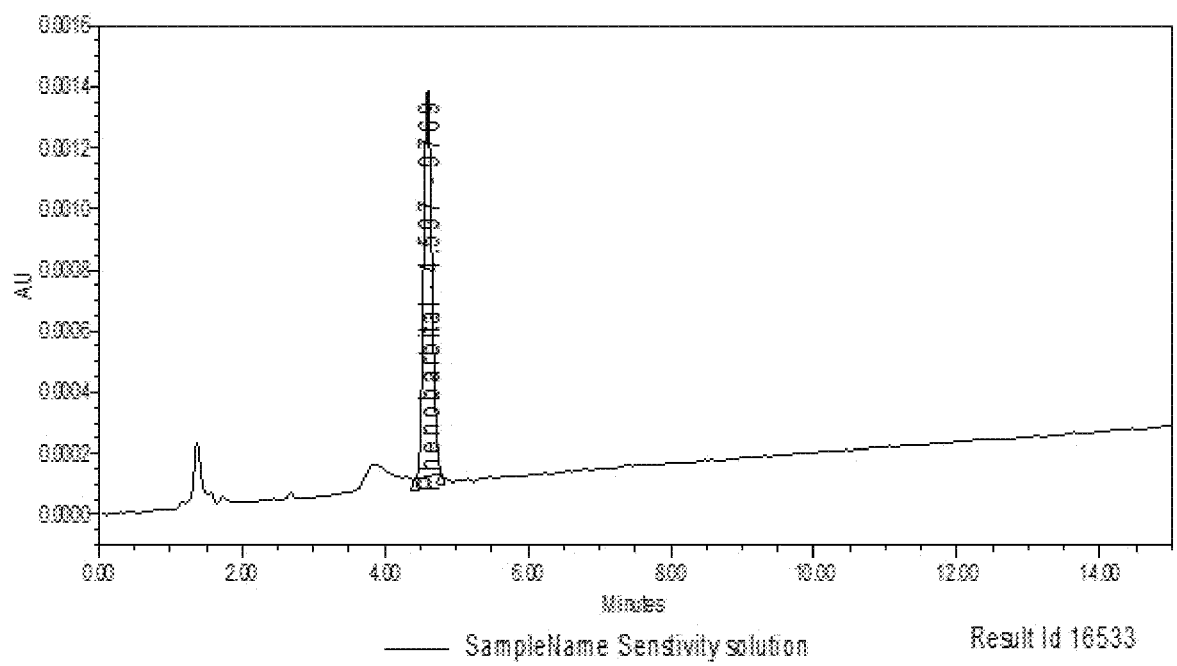
FIG. 2B is a chromatogram from an injection of the "Sensitivity solution" of Phenobarbital for related substances by HPLC at a detection wavelength of 210 nm, as described herein.
Figure 2C:
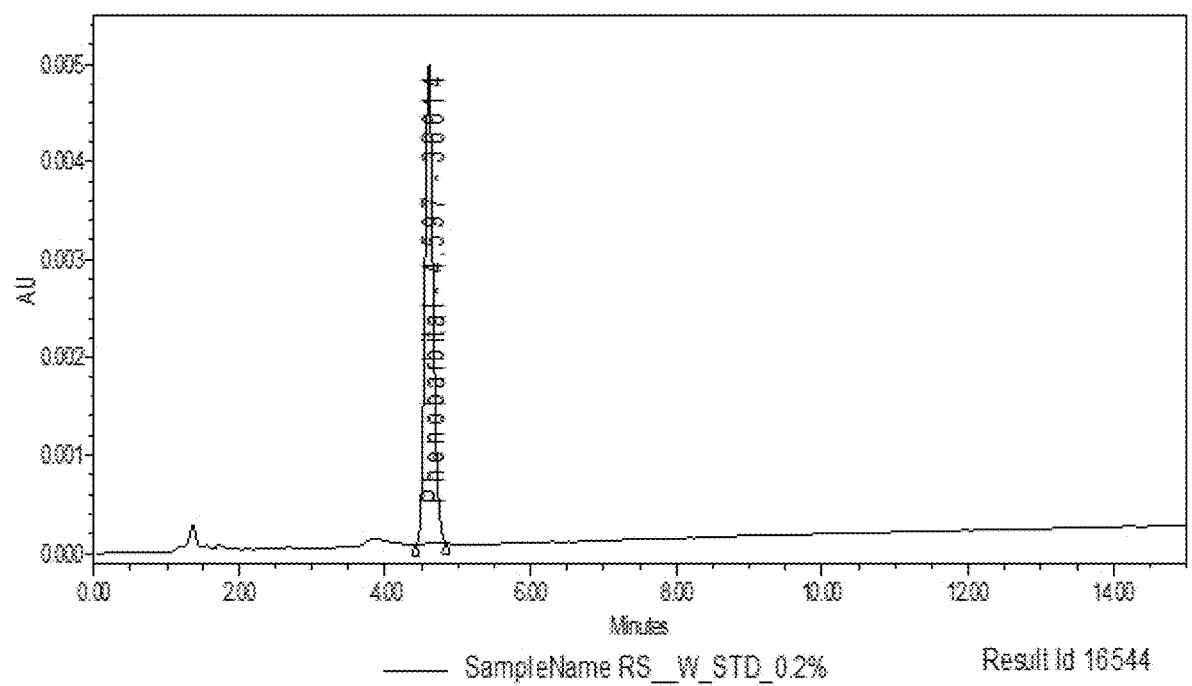
FIG. 2C is a chromatogram from an injection of a "related substance" (RS) working standard at 0.2% impurity level) for assay of related substances by HPLC at a detection wavelength of 210 nm, as described herein.
Figure 2D:
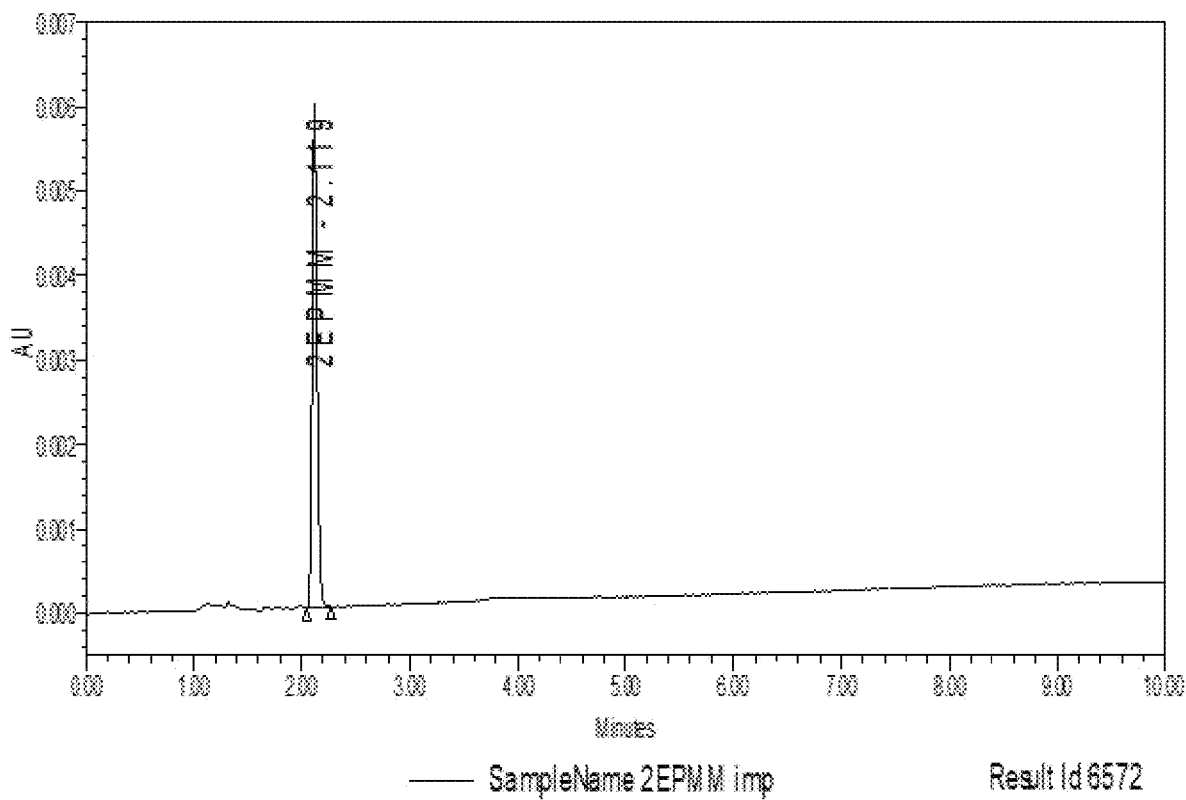
FIG. 2D is a chromatogram from an injection of 2-ethyl-2-phenylmalonamide (2EPMM) for assay of related substances by HPLC at a detection wavelength of 210 nm, as described herein.
Figure 2E:
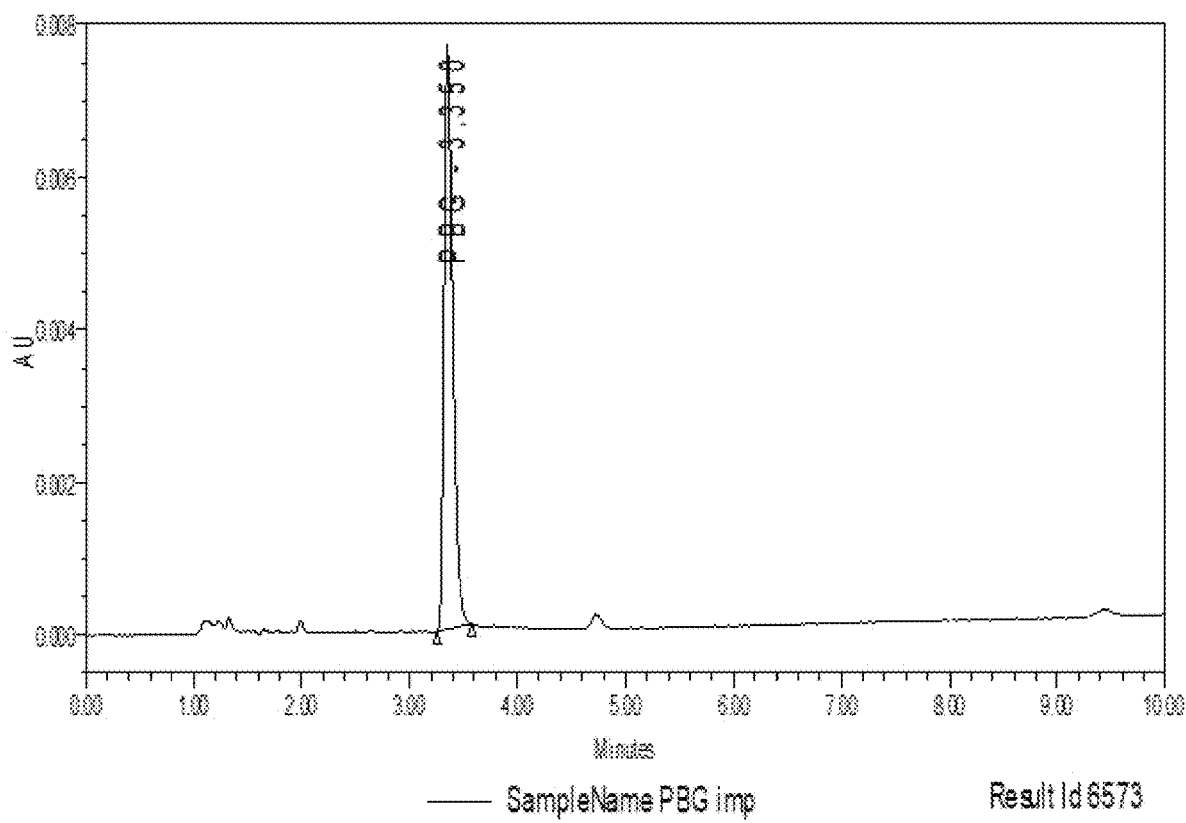
FIG. 2E is a chromatogram from an injection of alpha-phenylbutyrylguanidine (PBG) for assay of related substances by HPLC at a detection wavelength of 210 nm, as described herein.
Figure 2F:
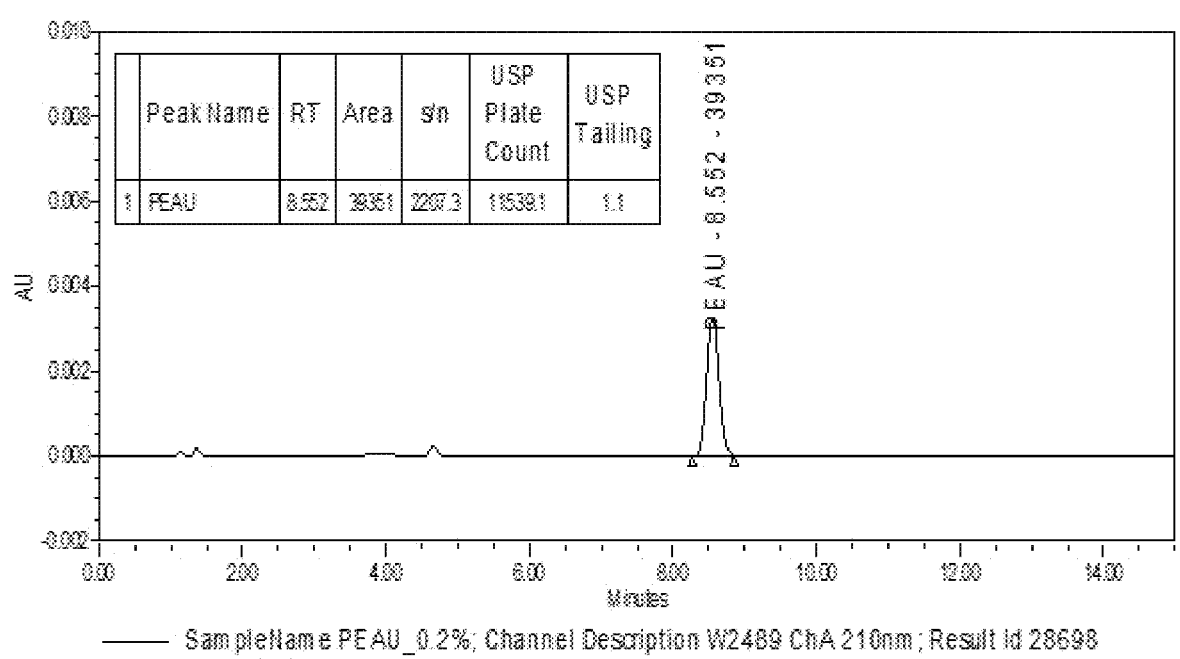
FIG. 2F is a chromatogram from an injection of phenylethylacetylurea (PEAU) for assay of related substances by HPLC at a detection wavelength of 210 nm, as described herein.
Figure 2G:
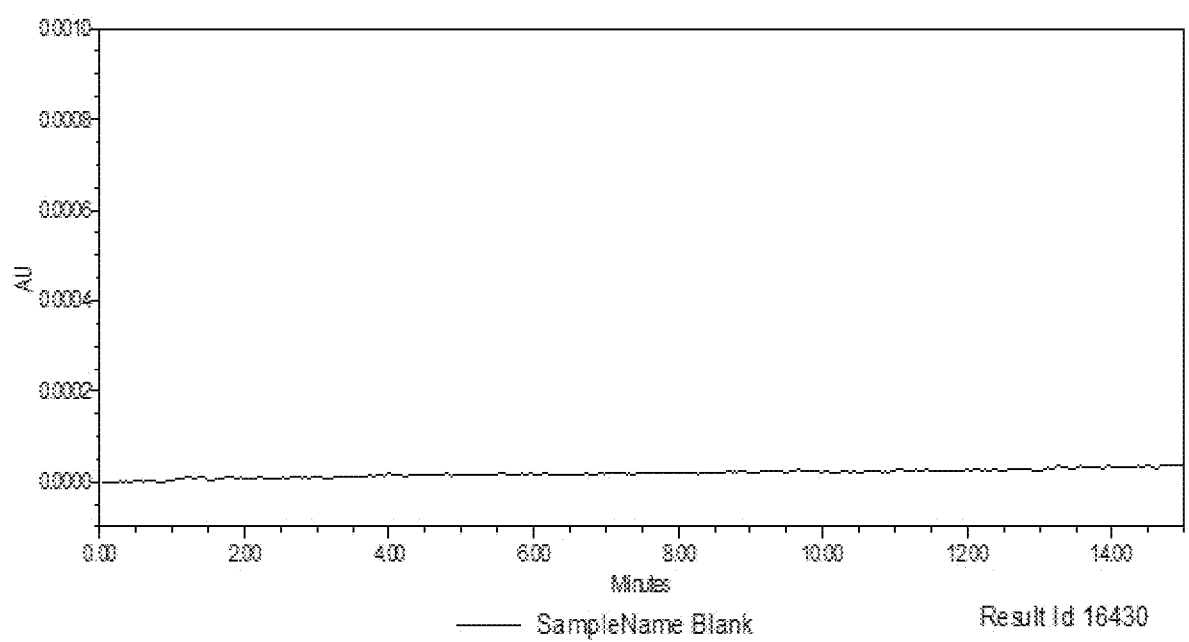
FIG. 2G is a chromatogram from an injection of a "blank solution" for assay by HPLC at a detection wavelength of 254 nm, as described herein.
Figure 2H:
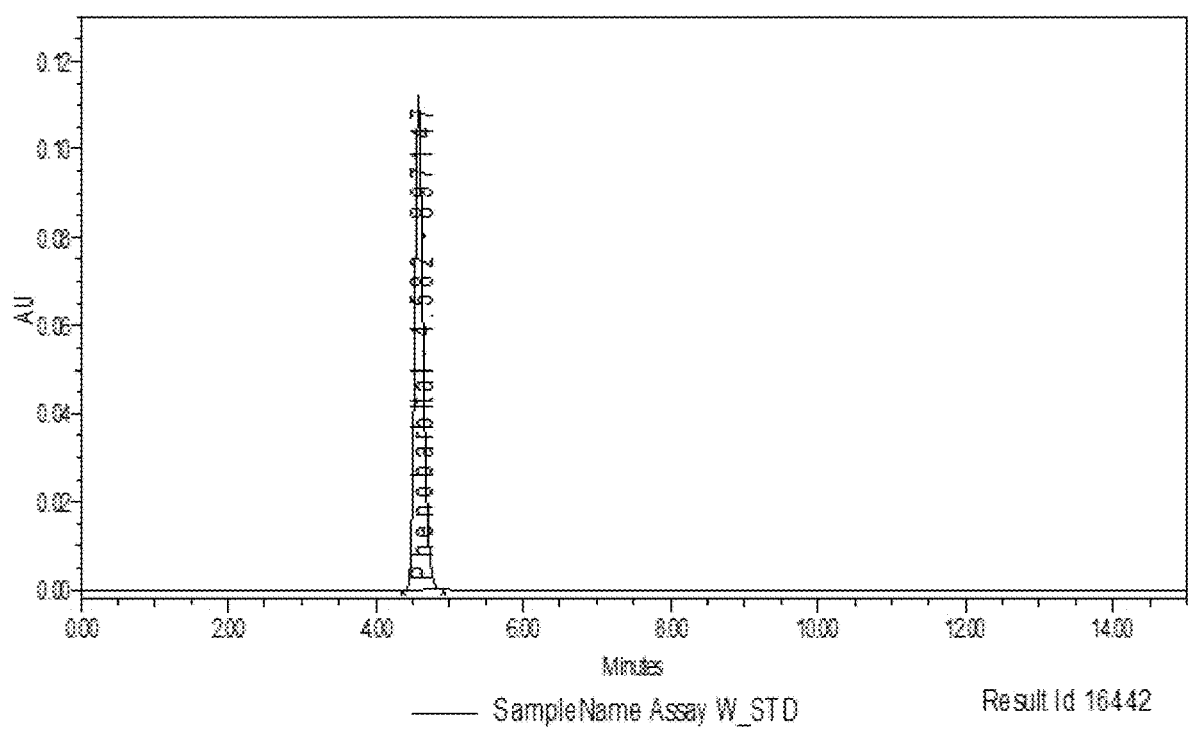
FIG. 2H is a chromatogram from an injection of an "assay working standard" for assay by HPLC at a detection wavelength of 254 nm, as described herein.
Figure 3A:
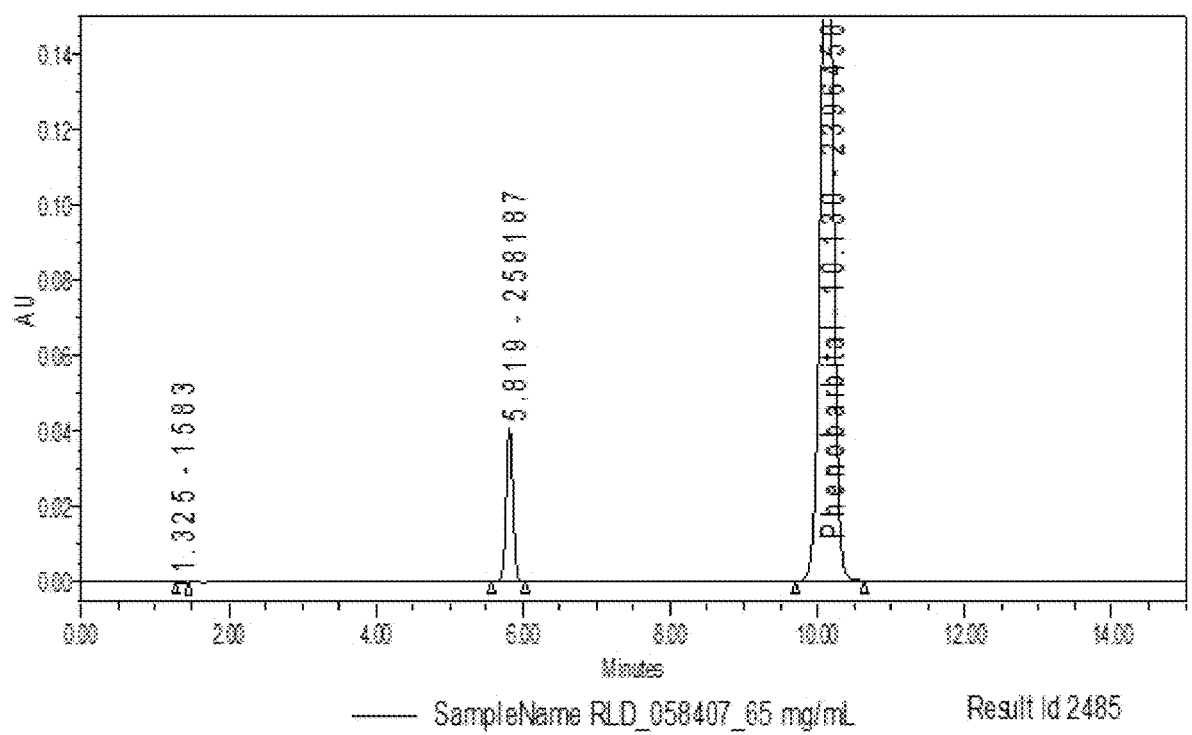
FIG. 3A is a chromatogram from an injection of a marketed liquid formulation of Phenobarbital Sodium at 65 mg/mL at initial time point for assay by HPLC at a detection wavelength of 254 nm, as described herein.
Figure 3B:
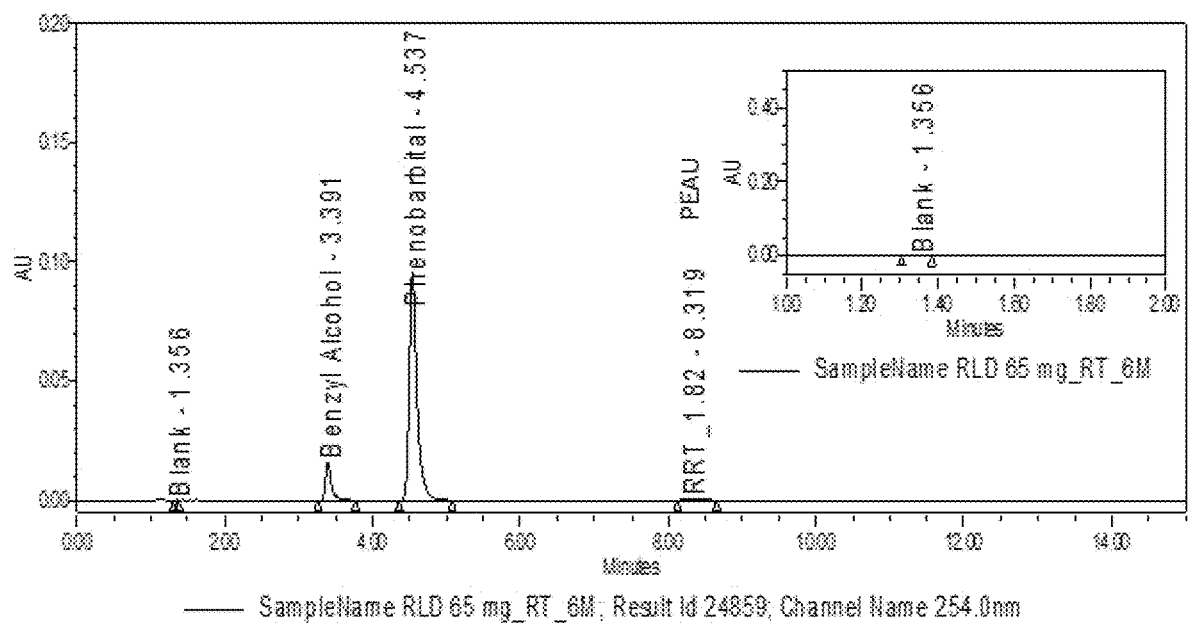
FIG. 3B is a chromatogram from an injection of a marketed liquid formulation of Phenobarbital Sodium at 65 mg/mL at 6 months from initial time point at room temperature (RT) for assay by HPLC at a detection wavelength of 254 nm, as described herein.
Figure 3C:
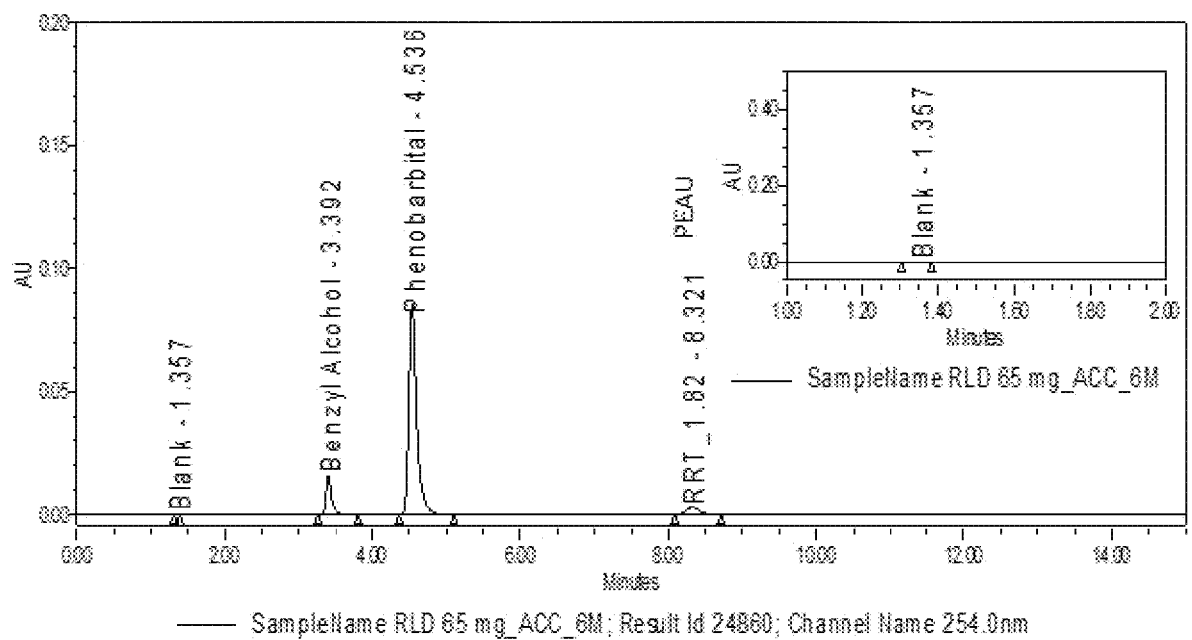
FIG. 3C is a chromatogram from an injection of a marketed liquid formulation of Phenobarbital Sodium at 65 mg/mL at 6 months from initial time point at accelerated stability conditions (ACC) for assay by HPLC at a detection wavelength of 254 nm, as described herein.
Figure 3D:
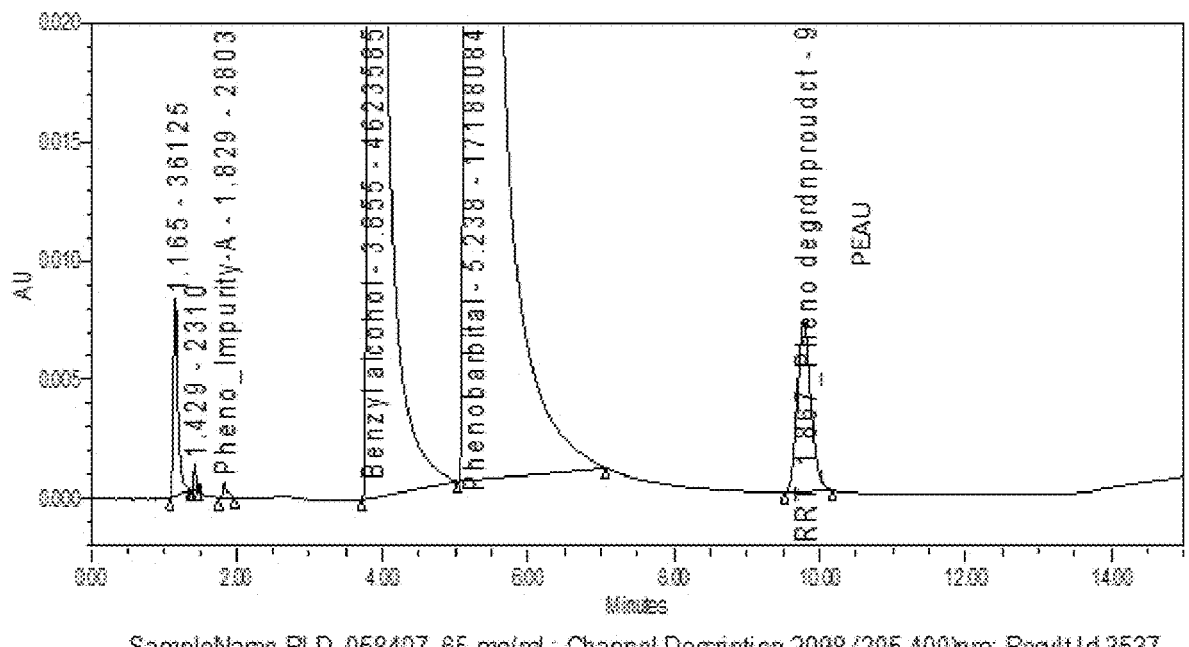
FIG. 3D is a chromatogram from an injection of a marketed liquid formulation of Phenobarbital Sodium at 65 mg/mL at initial time point for related substances by HPLC at a detection wavelength of 210 nm, as described herein.
Figure 3E:
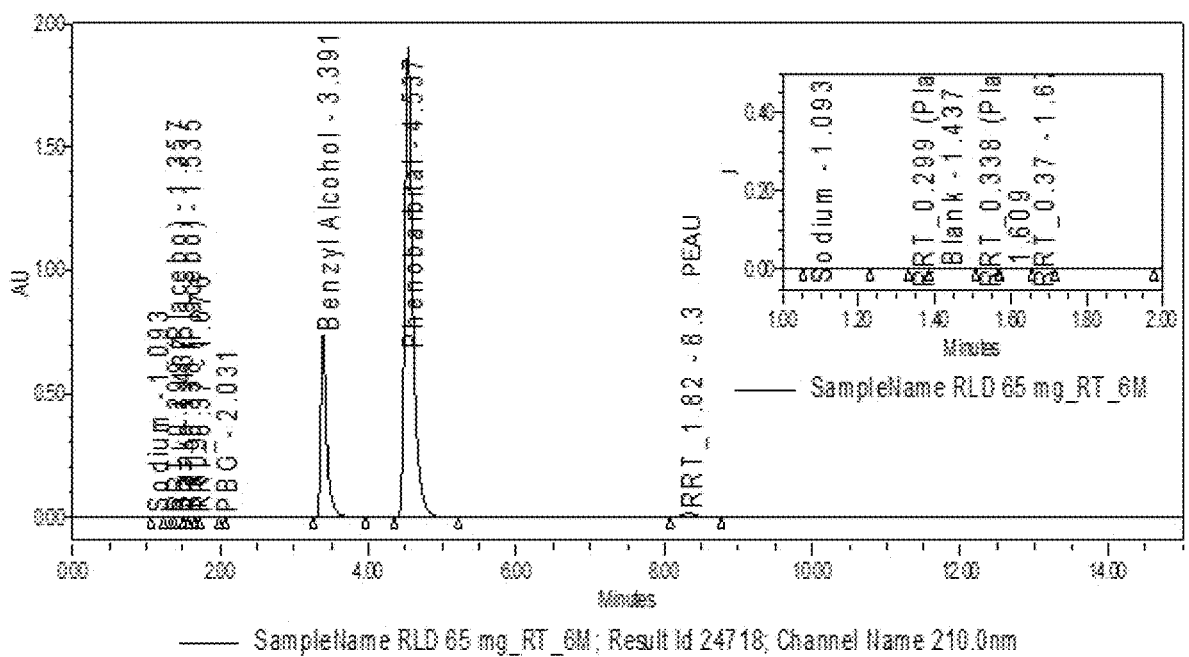
FIG. 3E is a chromatogram from an injection of a marketed liquid formulation of Phenobarbital Sodium at 65 mg/mL at 6 months from initial time point at room temperature (RT) for related substances by HPLC at a detection wavelength of 210 nm, as described herein.
Figure 3F:
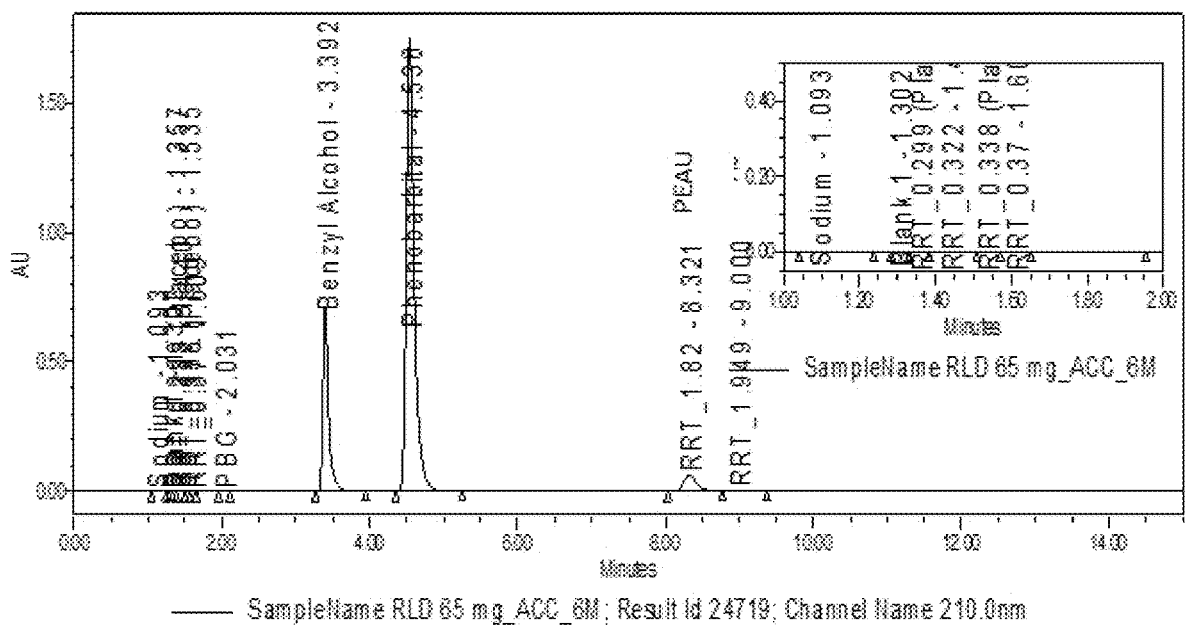
FIG. 3F is a chromatogram from an injection of a marketed liquid formulation of Phenobarbital Sodium at 65 mg/mL at 6 months from initial time point at accelerated stability conditions (ACC) for related substances by HPLC at a detection wavelength of 210 nm, as described herein.
Figure 3G:
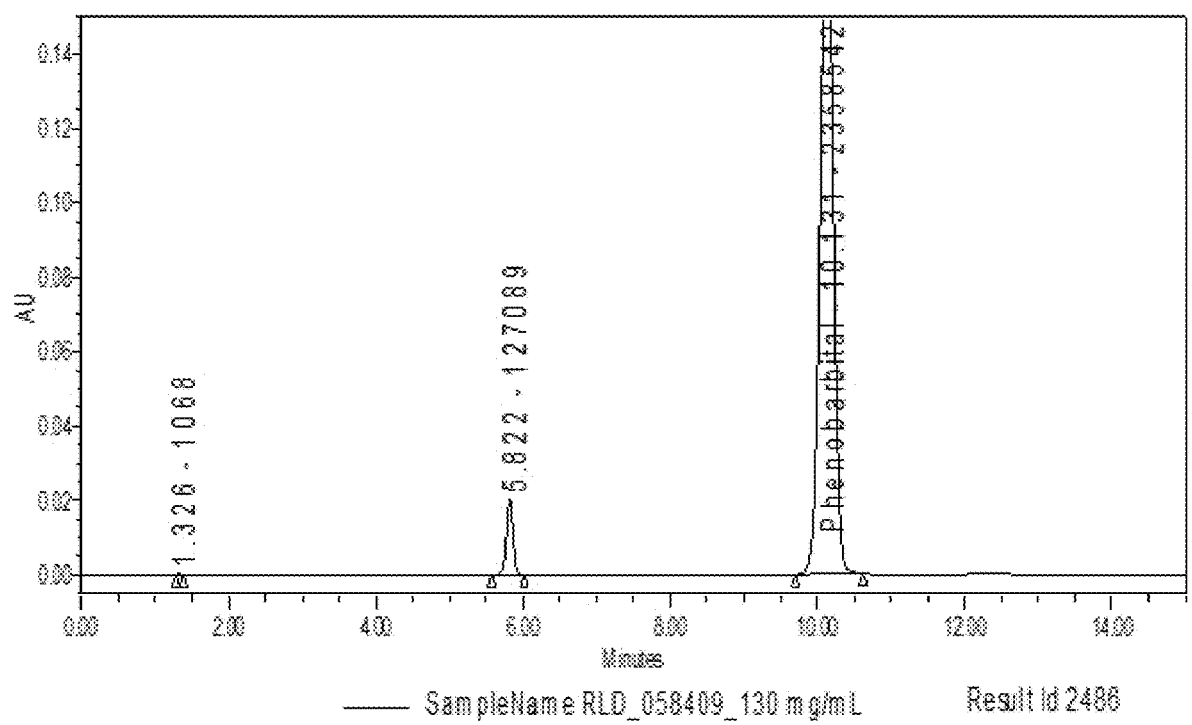
FIG. 3G is a chromatogram from an injection of a marketed liquid formulation of Phenobarbital Sodium at 130 mg/mL at initial time point for assay by HPLC at a detection wavelength of 254 nm, as described herein.
Figure 3H:
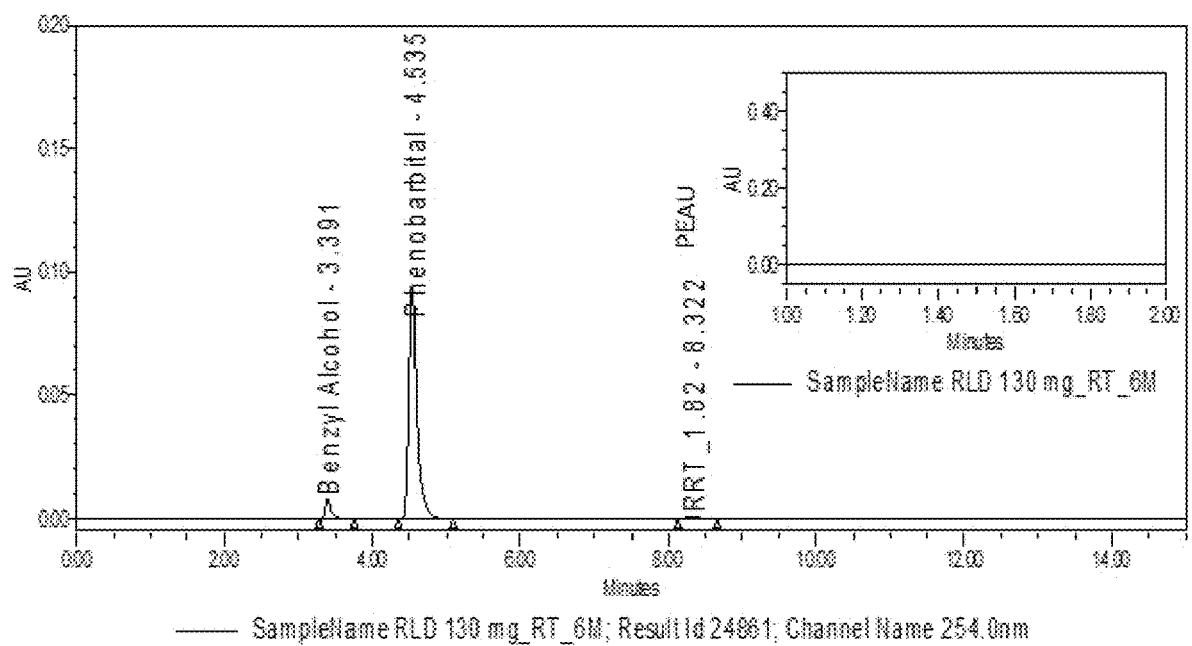
FIG. 3H is a chromatogram from an injection of a marketed liquid formulation of Phenobarbital Sodium at 130 mg/mL at 6 months from initial time point at room temperature (RT) for assay by HPLC at a detection wavelength of 254 nm, as described herein.
Figure 3I:
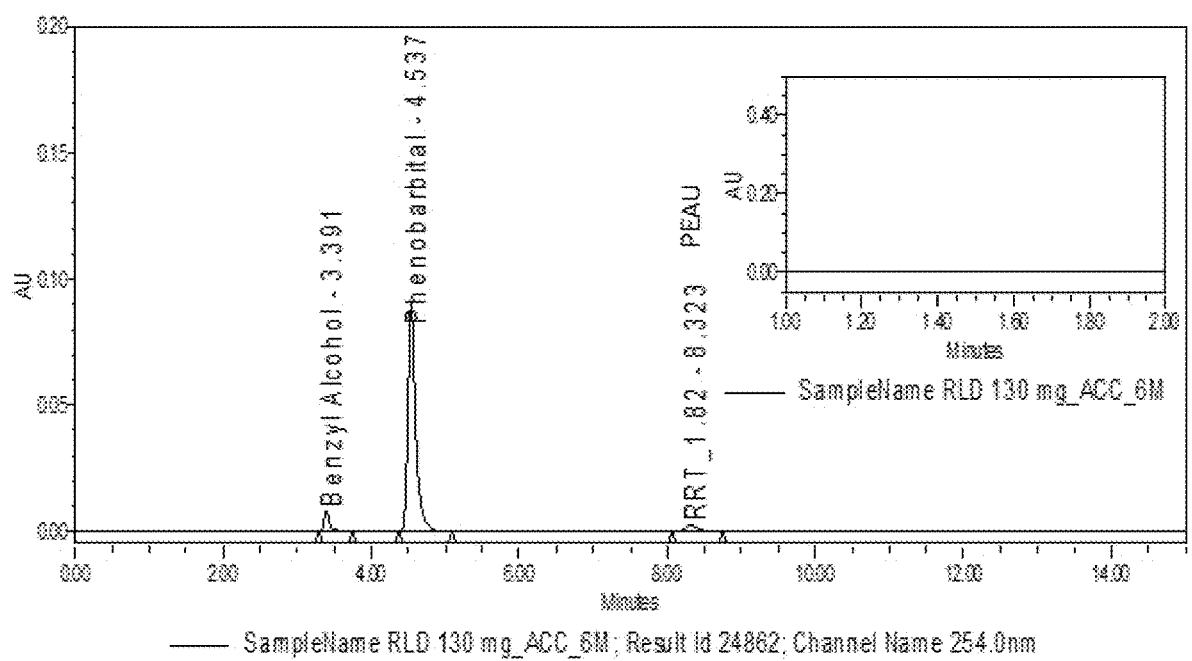
FIG. 3I is a chromatogram from an injection of a marketed liquid formulation of Phenobarbital Sodium at 130 mg/mL at 6 months from initial time point at accelerated stability conditions (ACC) for assay by HPLC at a detection wavelength of 254 nm, as described herein.
Figure 3J:
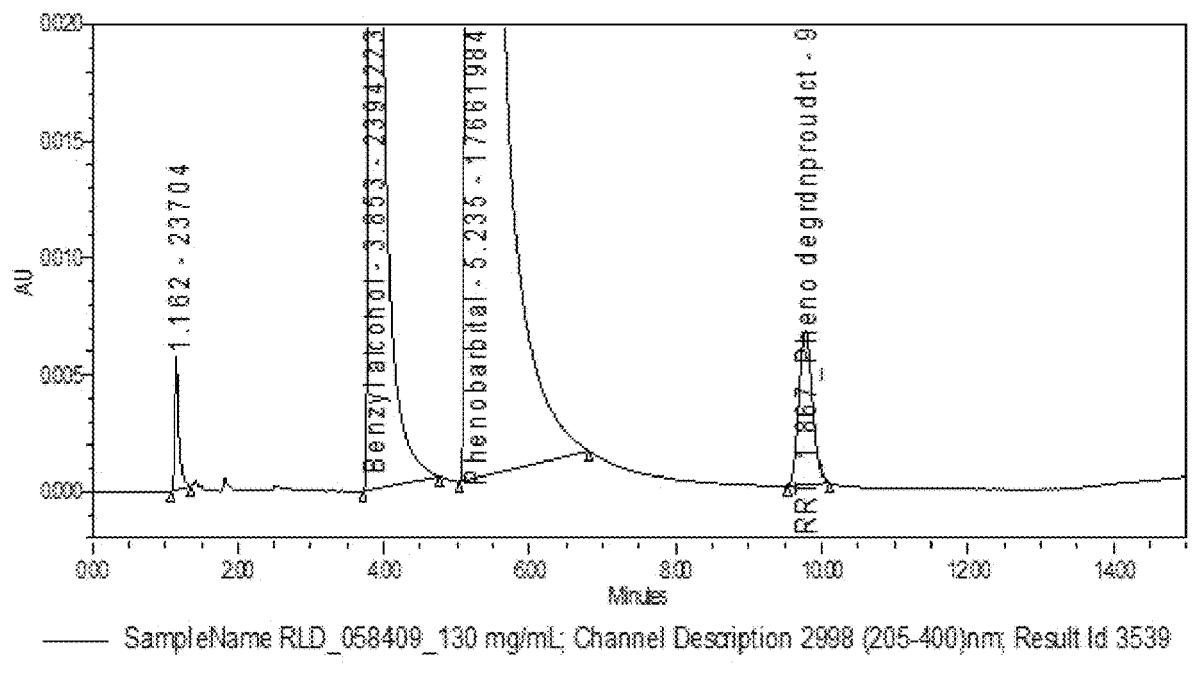
FIG. 3J is a chromatogram from an injection of a marketed liquid formulation of Phenobarbital Sodium at 130 mg/mL at initial time point for related substances by HPLC at a detection wavelength of 210 nm, as described herein.
Figure 3K:
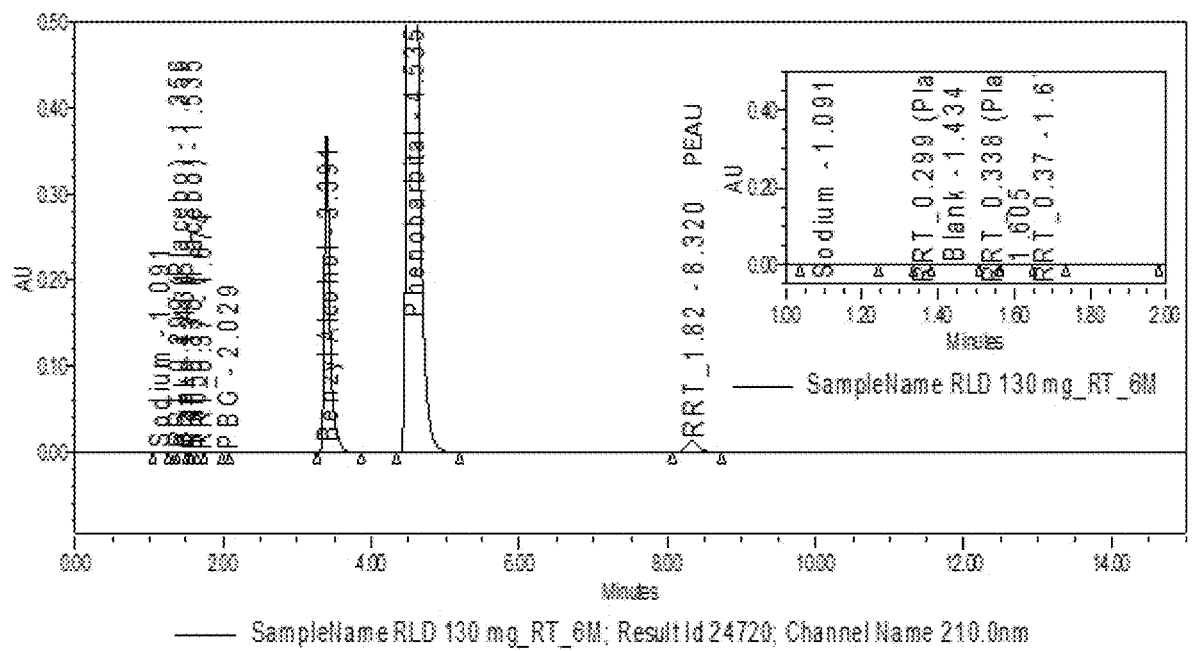
FIG. 3K is a chromatogram from an injection of a marketed liquid formulation of Phenobarbital Sodium at 130 mg/mL at 6 months from initial time point at room temperature (RT) for related substances by HPLC at a detection wavelength of 210 nm, as described herein.
Figure 3L:
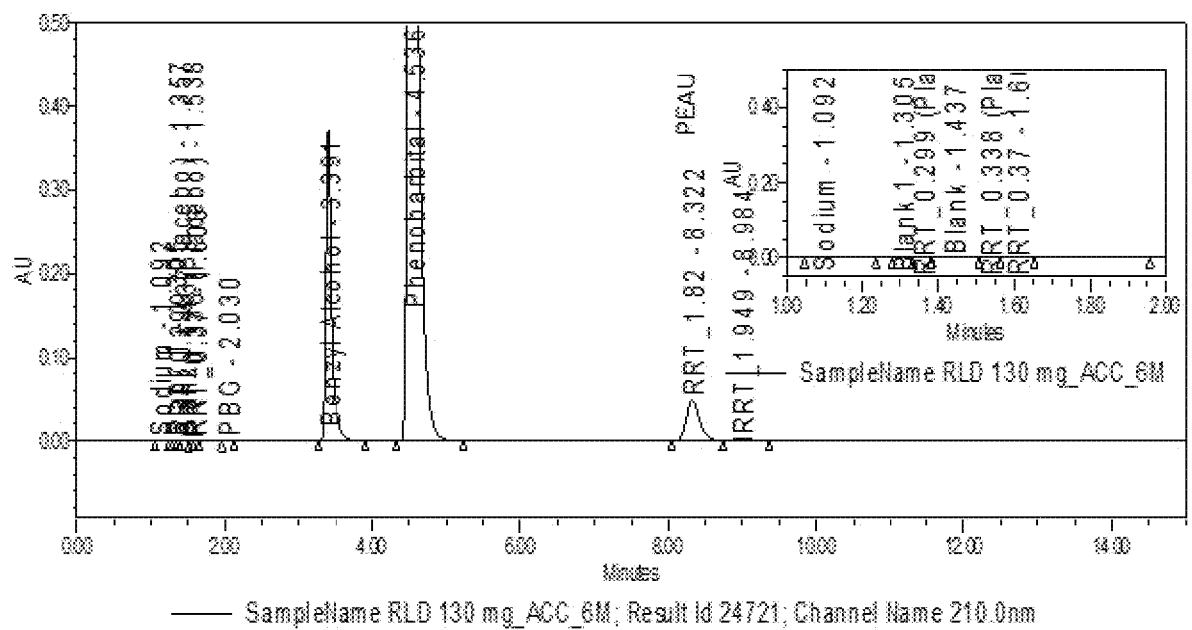
FIG. 3L is a chromatogram from an injection of a marketed liquid formulation of Phenobarbital Sodium at 130 mg/mL at 6 months from initial time point at accelerated stability conditions (ACC) for related substances by HPLC at a detection wavelength of 210 nm, as described herein.
Figure 4A:
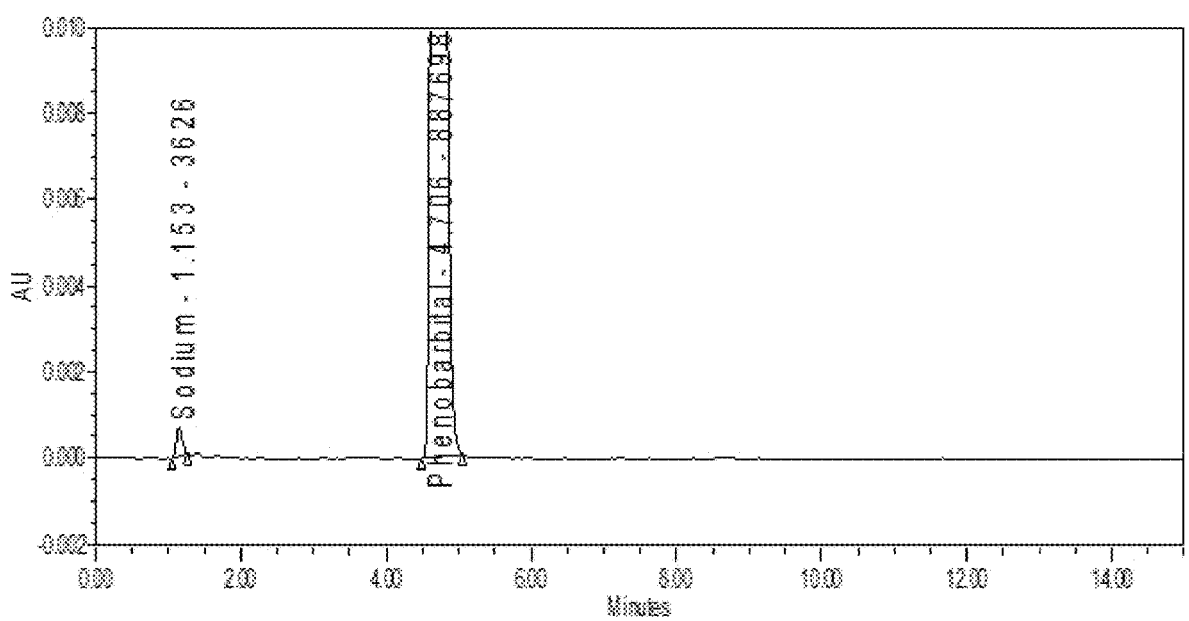
FIG. 4A is a chromatogram from an injection of the disclosed reconstituted lyophilized formulation of Phenobarbital Sodium at 65 mg/mL at initial time point for assay by HPLC at a detection wavelength of 254 nm, according to embodiments of the present invention.
Figure 4B:
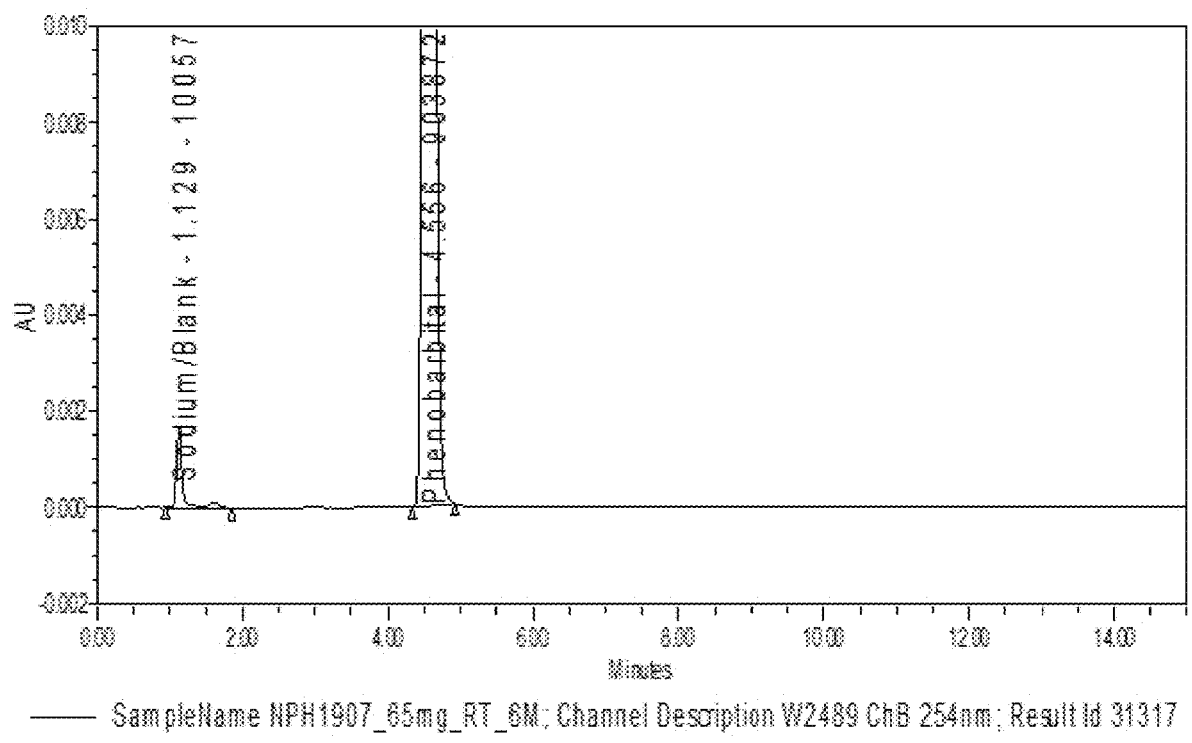
FIG. 4B is a chromatogram from an injection of the disclosed reconstituted lyophilized formulation of Phenobarbital Sodium at 65 mg/mL at 6 months from initial time point at room temperature (RT) for assay by HPLC at a detection wavelength of 254 nm, according to embodiments of the present invention.
Figure 4C:
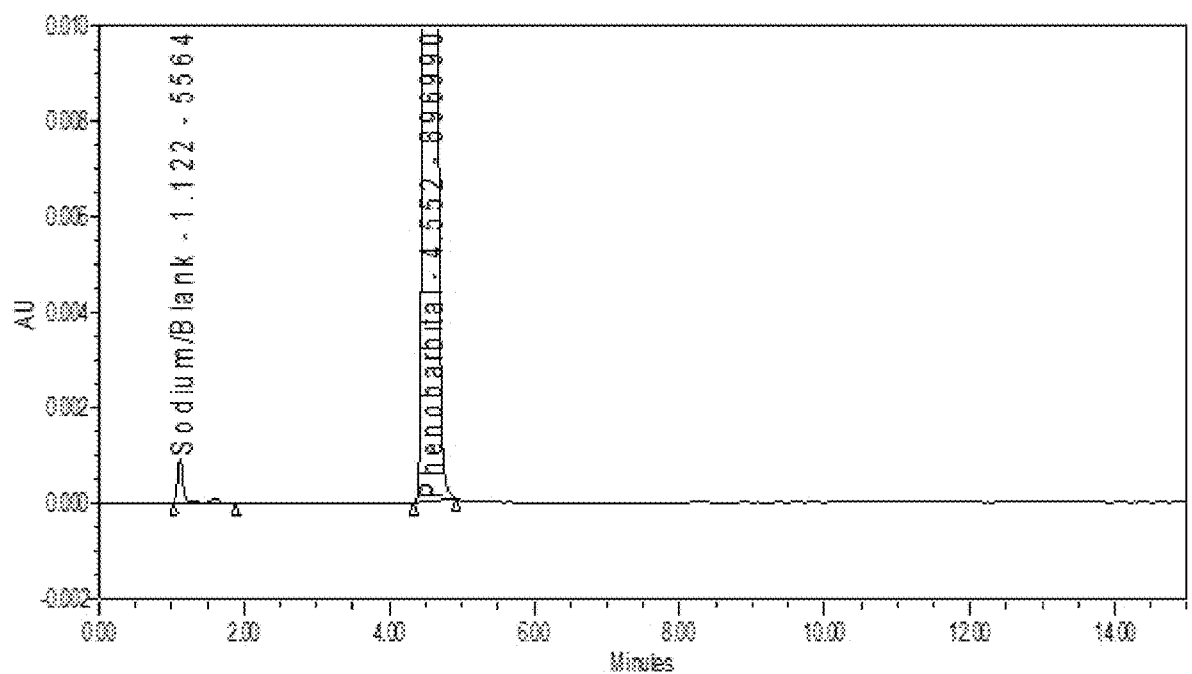
FIG. 4C is a chromatogram from an injection of the disclosed reconstituted lyophilized formulation of Phenobarbital Sodium at 65 mg/mL at 6 months from initial time point at accelerated stability conditions (ACC) for assay by HPLC at a detection wavelength of 254 nm, according to embodiments of the present invention.
Figure 4D:
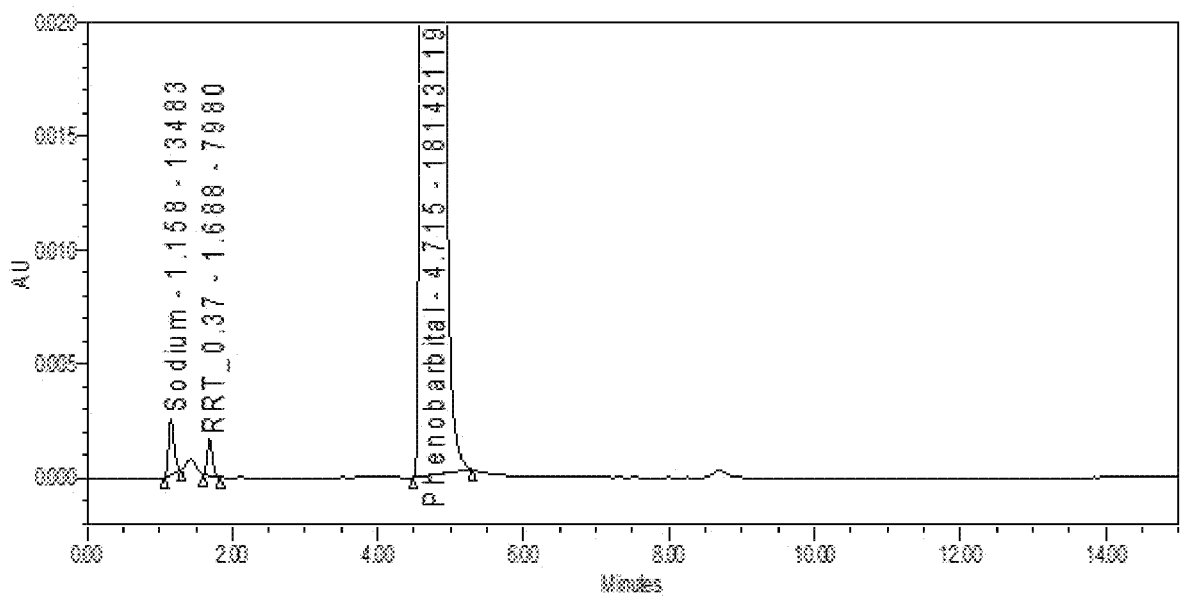
FIG. 4D is a chromatogram from an injection of the disclosed reconstituted lyophilized formulation of Phenobarbital Sodium at 65 mg/mL at initial time point for related substances by HPLC at a detection wavelength of 210 nm, according to embodiments of the present invention.
Figure 4E:
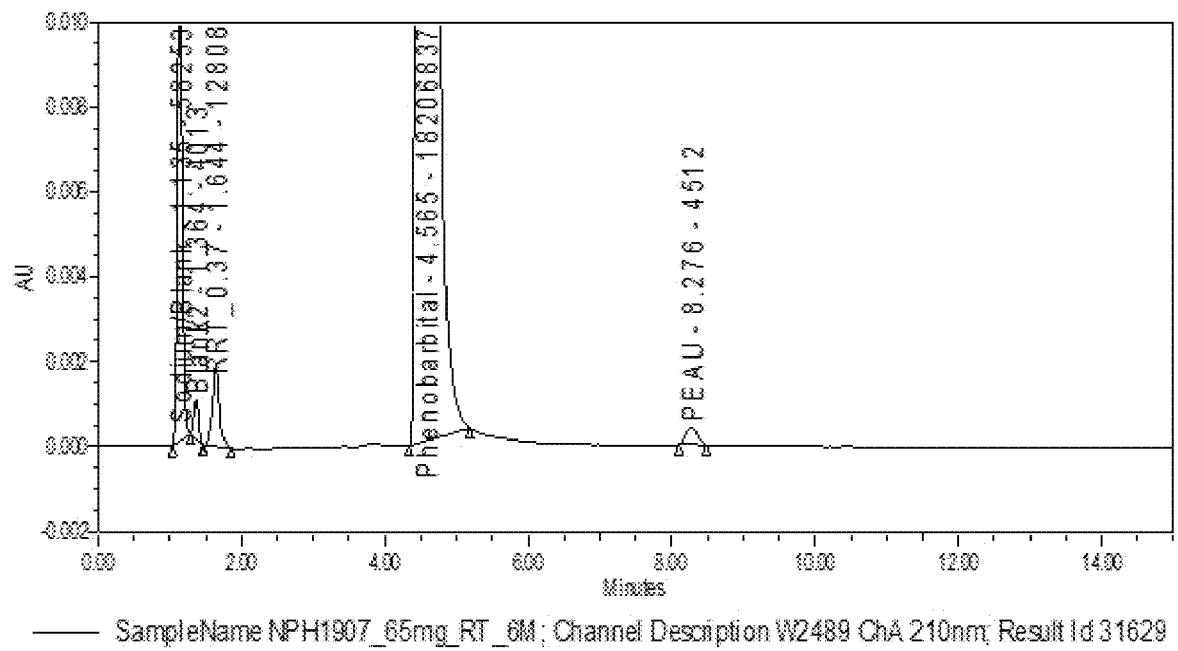
FIG. 4E is a chromatogram from an injection of the disclosed reconstituted lyophilized formulation of Phenobarbital Sodium at 65 mg/mL at 6 months from initial time point at room temperature (RT) for related substances by HPLC at a detection wavelength of 210 nm, according to embodiments of the present invention.
Figure 4F:
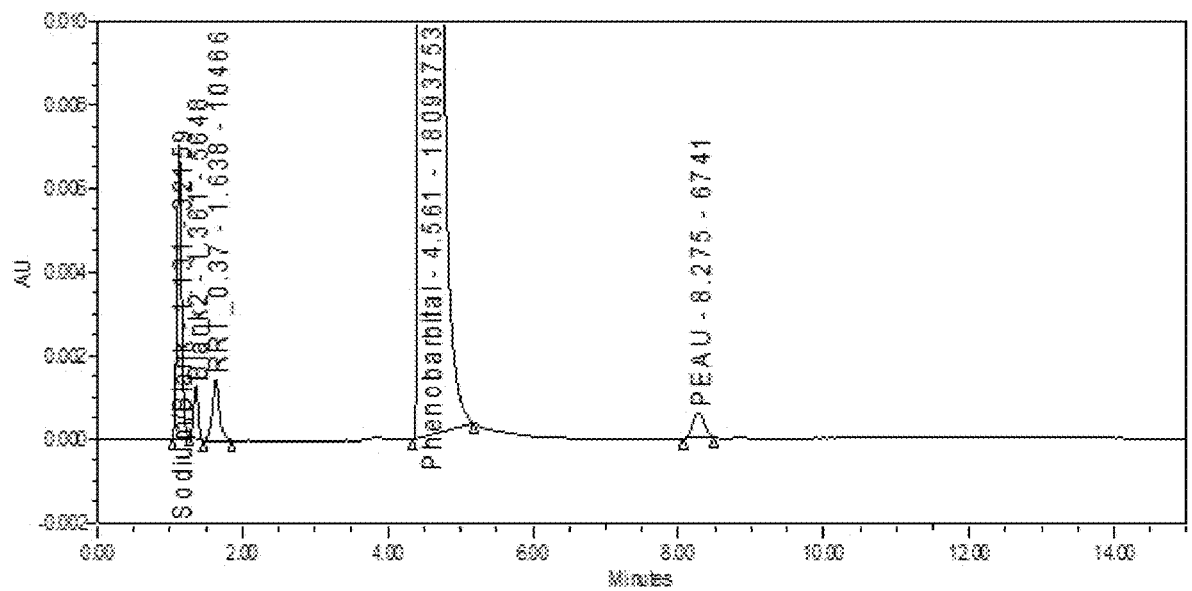
FIG. 4F is a chromatogram from an injection of the disclosed reconstituted lyophilized formulation of Phenobarbital Sodium at 65 mg/mL at 6 months from initial time point at accelerated stability conditions (ACC) for related substances by HPLC at a detection wavelength of 210 nm, according to embodiments of the present invention.
Figure 4G:
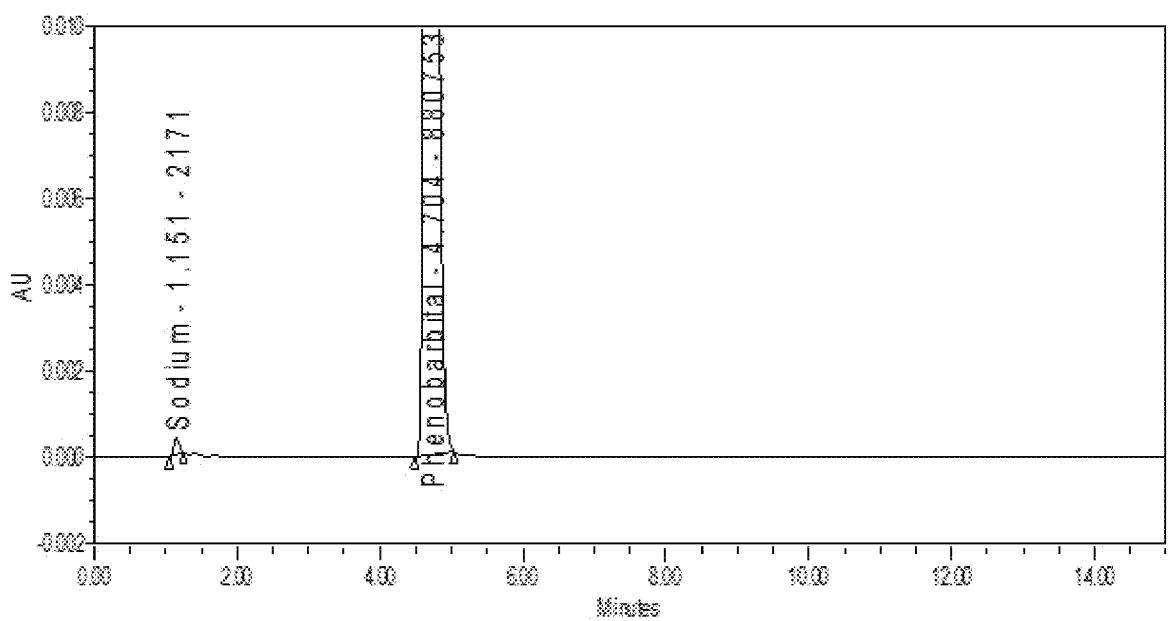
FIG. 4G is a chromatogram from an injection of the disclosed reconstituted lyophilized formulation of Phenobarbital Sodium at 130 mg/mL at initial time point for assay by HPLC at a detection wavelength of 254 nm, according to embodiments of the present invention.
Figure 4H:
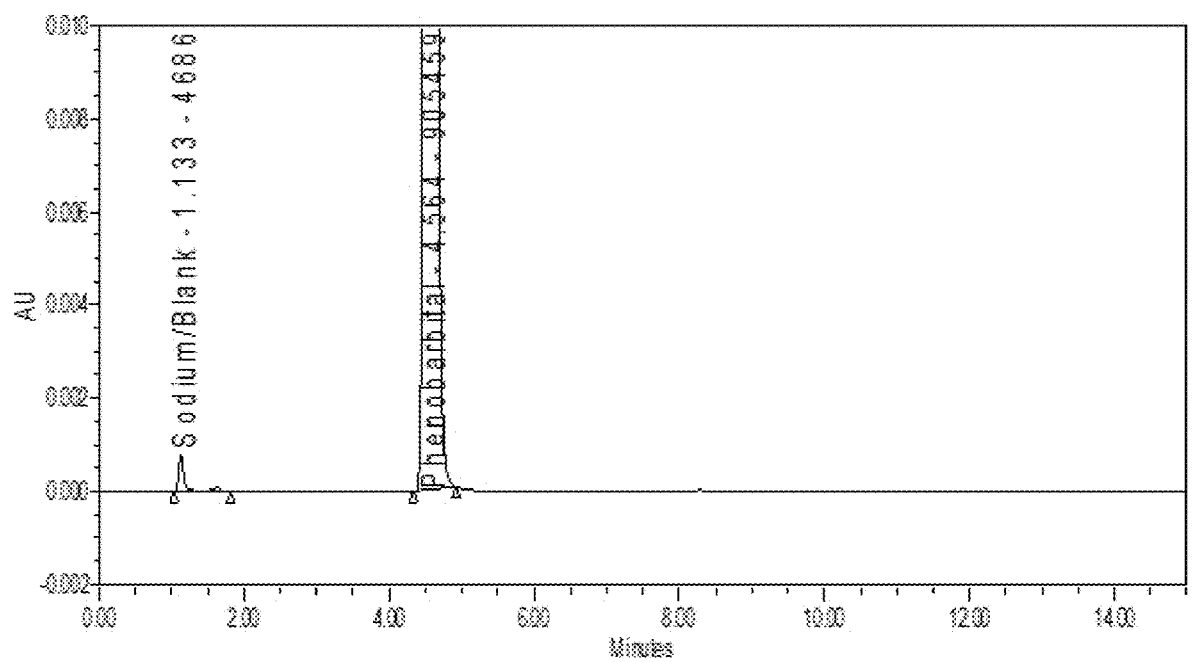
FIG. 4H is a chromatogram from an injection of the disclosed reconstituted lyophilized formulation of Phenobarbital Sodium at 130 mg/mL at 6 months from initial time point at room temperature (RT) for assay by HPLC at a detection wavelength of 254 nm, according to embodiments of the present invention.
Figure 4I:
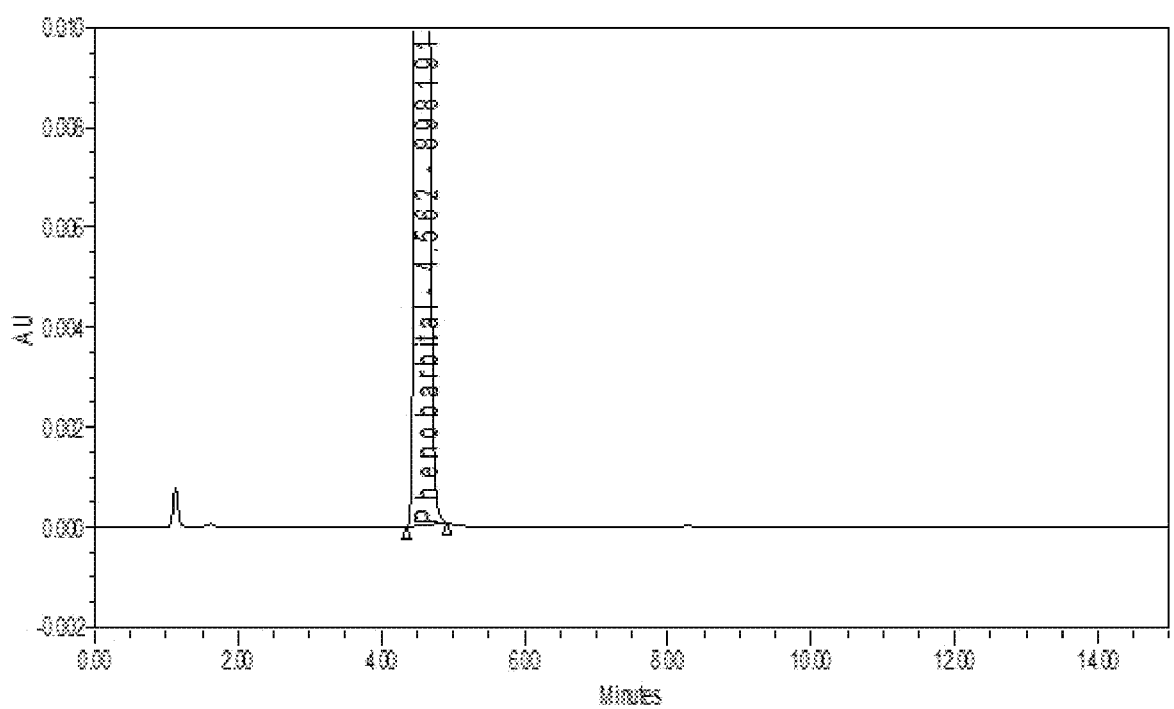
FIG. 4I is a chromatogram from an injection of the disclosed reconstituted lyophilized formulation of Phenobarbital Sodium at 130 mg/mL at 6 months from initial time point at accelerated stability conditions (ACC) for assay by HPLC at a detection wavelength of 254 nm, according to embodiments of the present invention.
Figure 4J:
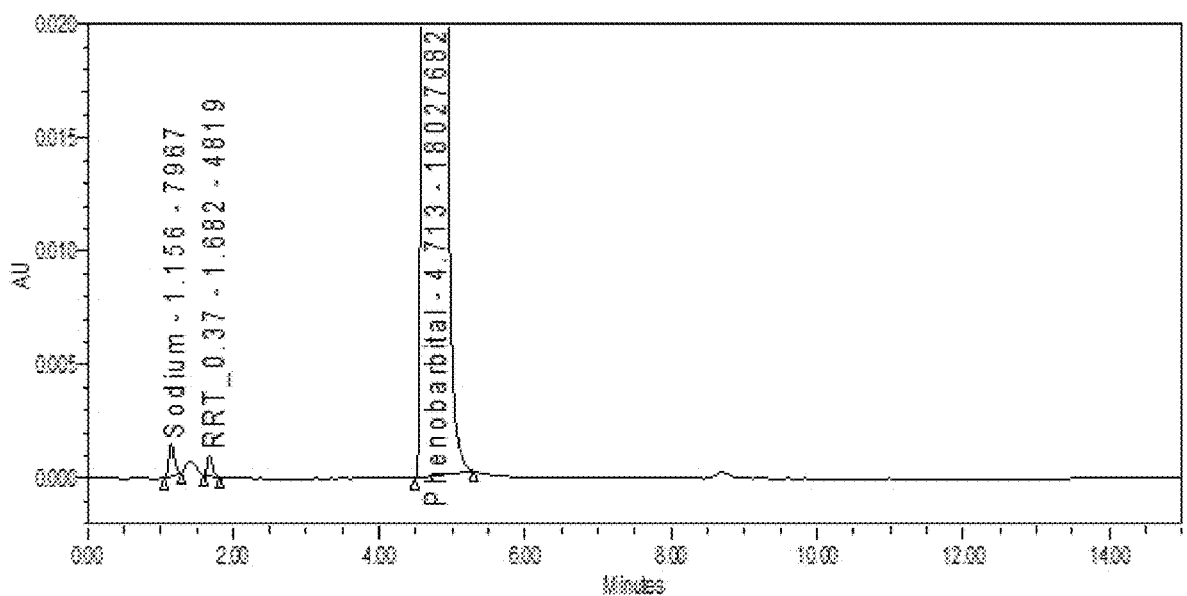
FIG. 4J is a chromatogram from an injection of the disclosed reconstituted lyophilized formulation of Phenobarbital Sodium at 130 mg/mL at initial time point for related substances by HPLC at a detection wavelength of 210 nm, according to embodiments of the present invention.
Figure 4K:
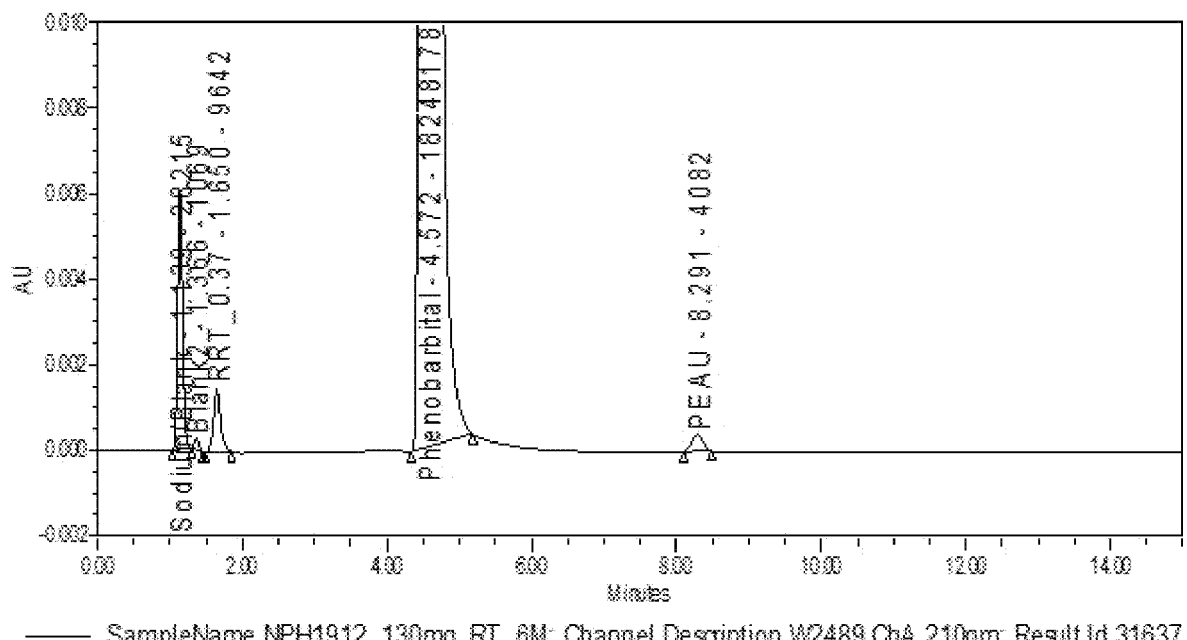
FIG. 4K is a chromatogram from an injection of the disclosed reconstituted lyophilized formulation of Phenobarbital Sodium at 130 mg/mL at 6 months from initial time point at room temperature (RT) for related substances by HPLC at a detection wavelength of 210 nm, according to embodiments of the present invention.
Figure 4L:
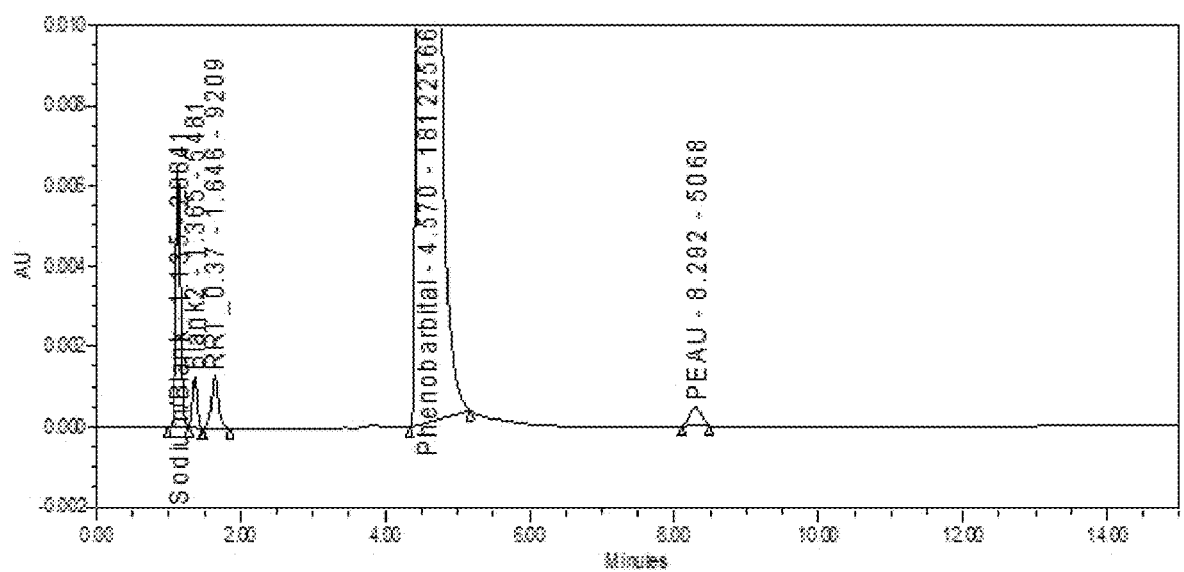
FIG. 4L is a chromatogram from an injection of the disclosed reconstituted lyophilized formulation of Phenobarbital Sodium at 130 mg/mL at 6 months from initial time point at accelerated stability conditions (ACC) for related substances by HPLC at a detection wavelength of 210 nm, according to embodiments of the present invention.
Figure 5A:
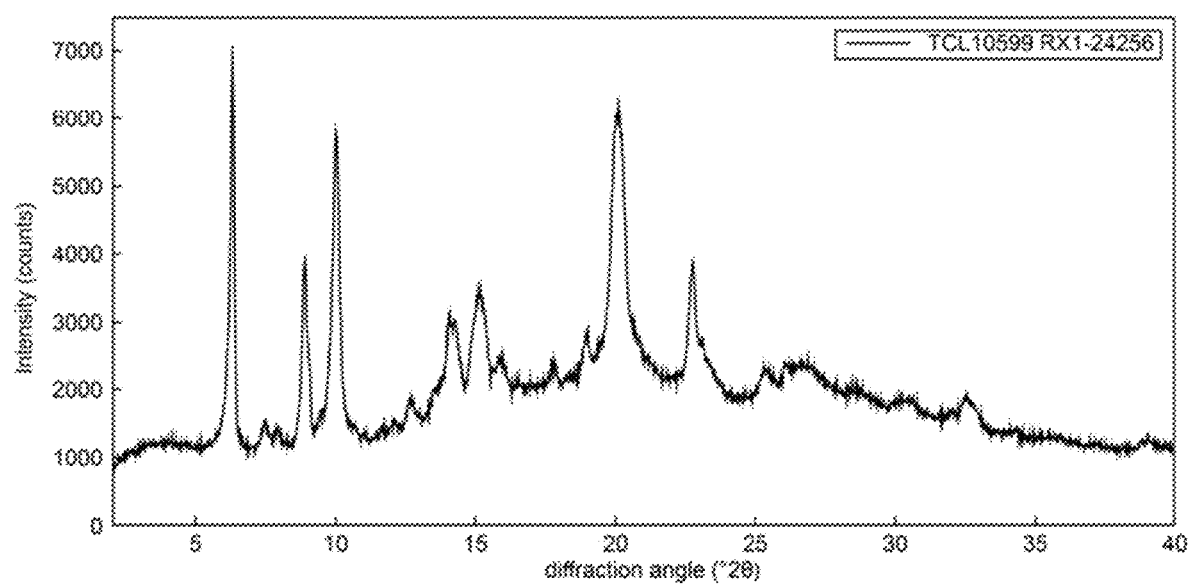
FIG. 5A is an X-ray powder diffraction (XRPD) pattern of Phenobarbital Sodium Grade P

The contemplated method for producing a storage-stable lyophilized Phenobarbital Sodium composition includes adding purified Phenobarbital Sodium to water. Preferably the purified Phenobarbital Sodium solid is purchased from a chemical supplier (e.g., Siegfried, USA) that adheres to the United States Pharmacopeia (USP) manufacturing and synthesis guidelines. The USP grade of the Phenobarbital Sodium is preferably USP "purified" or "practical" (P) grade indicating that it is a good quality chemical. As understood in the art, the USP grade (P) active pharmaceutical ingredient (API) of Phenobarbital Sodium is not suitable for administration because it is not sterile, is hygroscopic, and as such, maintaining anhydrous conditions of this grade of API is not feasible. Structurally, the analyzed USP grade P API (Siegfried, USA) is polymorphous—containing both crystalline and non-crystalline material. With reference to FIG. 5A, an X-ray powder diffraction (XRPD) pattern is shown of this compound.

Considering the need to avoid hydrolysis of the Phenobarbital Sodium, the Phenobarbital Sodium is preferably added to Water for Injection and later lyophilized to obtain a stable lyophilized finished product. In order to remove dissolved oxygen ($O_2$) gas from the water (e.g., Water for Injection), it is also preferred that the water is sparged with nitrogen ($N_2$) or other inert gas prior to the addition of the Phenobarbital Sodium solid. For effective sparging, a volume of about 100-200 ml water is sparged with nitrogen gas for at least 30 minutes. In exemplary protocols for producing either 65 mg, 130 mg of lyophilized Phenobarbital Sodium, 100 milliliters (ml) of Water for Injection is nitrogen sparged for 30 minutes. In additional embodiments, the water may also be cooled to approximately 2 to 8° C. In preferred embodiments, the water is cooled to approximately 2 to 8° C.

The addition of the Phenobarbital Sodium solid to the water (e.g., deionized nitrogen sparged water cooled to 2 to 8° C.) may be carried out using any suitable mixing. Preferably, the water (e.g., Water for Injection) is first added to a glass/stainless steel container for nitrogen sparging and cooling, and this prepped water remains in the glass/stainless steel container or a measured amount is transferred to a preferably weighed glass container/stainless steel container and the Phenobarbital Sodium solid is added thereto. For mixing, any suitable mixing may be used. For example, a magnetic stir bar may be added to the glass/stainless steel container. Upon addition of the Phenobarbital Sodium solid to the water, the mixture is stirred.

An additional consideration for stability of the Phenobarbital Sodium is maintaining a pH between 9.2 and 10.2 in the bulk solution of Phenobarbital Sodium. After dissolution of the Phenobarbital Sodium solid in the water, the pH is adjusted to within this range of 9.2 and 10.2. Accordingly, the pH of the water solubilized Phenobarbital Sodium is first measured upon dissolution. If the pH is higher than 10.2 or lower than 9.2, the pH is adjusted. For example, if necessary, the pH may be lowered to or between 9.2 and 10.2 using Hydrochloric acid (HCl) and the pH may be increased to or between 9.2 and 10.2 using Sodium Hydroxide (NaOH).

Following the pH measurement and any adjustment, the Phenobarbital Sodium solution is preferably filtered to remove any foreign particles. For example, the Phenobarbital Sodium solution may be filtered using a 0.2 μm (or 0.22 μm) membrane filter. For example, the membrane filter may be polyvinylidene difluoride (PVDF) or any other compatible filter membranes such as Polyethersulfone (PES) filter.

According to aspects of the contemplated method, the Phenobarbital Sodium solution dissolved in the water (e.g., nitrogen sparged Water for Injection cooled to 2 to 8° C.) having a pH of or between 9.2 and 10.2 and preferably filtered is ready for Lyophilization. Depending on the desired amount of the lyophilized Phenobarbital Sodium product, the Phenobarbital Sodium solution may be lyophilized in any amount or the solution may be aliquoted into sterile containers (e.g., vials). For example, in order to obtain a measured dose of lyophilized Phenobarbital Sodium in a container, the glass container, water, and Phenobarbital Sodium solid are weighed prior to mixing in order to determine an actual weight of the Phenobarbital Sodium after pH measurement and adjustment. For example, to produce 65 mg or 130 mg doses of lyophilized Phenobarbital Sodium, a batch may be dissolved, mixed, pH adjusted if necessary, and filtered and then aliquoted into single use dose vials for lyophilization. In a specific example, a 50 mL batch of Phenobarbital Sodium solution may be prepared where for 65 mg doses, 3.25 grams of Phenobarbital Sodium solid (e.g., USP Grade P) is added to 40 ml of water (e.g., nitrogen sparged Water for Injection cooled to 5 to 8° C.) and for 130 mg doses, 6.5 grams of the Phenobarbital Sodium is added to the 40 ml of water. Following dissolution, pH adjustment if necessary, adjusting final volume to 50.0 mL and filtering, 1 ml aliquots of this Phenobarbital Sodium solution are added to open (e.g., unstoppered) vials and then loosely stoppered (e.g., with lyophilization rubber stoppers) prior to lyophilization. Following lyophilization, each vial contains 65 mg or 130 mg of lyophilized Phenobarbital Sodium.

In further embodiments, following lyophilization, the vials may be completely closed (e.g., stoppered) under vacuum.

Another embodiment is directed to a pharmaceutical composition that consists of lyophilized amorphous Phenobarbital Sodium.

Another embodiment is directed to a method of producing a storage-stable form of lyophilized Phenobarbital sodium that forms no more than 0.2% phenylethylacetylurea (PEAU) when reconstituted in an aqueous solution. The method comprising: includes adding Phenobarbital Sodium to water to form a Phenobarbital Sodium solution, if necessary, adjusting the pH of the Phenobarbital Sodium solution to or between 9.2 to 10.2; and lyophilizing the Phenobarbital Sodium solution.

In one embodiment, the water is Water for Injection.

In another embodiment the Water for Injection is sparged with nitrogen prior to adding the Phenobarbital Sodium.

In another embodiment, the Water for Injection is sparged with nitrogen for at least 30 minutes prior to adding the Phenobarbital Sodium.

In another embodiment, the water is cooled to or between 2 to 8° C. prior to adding the Phenobarbital Sodium.

In another embodiment, the adjusting includes measuring the pH of the Phenobarbital Sodium solution, and if the pH is higher than 10.2, the adjusting includes adding Hydrochloric acid (HCl).

In another embodiment, the lyophilized Phenobarbital Sodium forms no more than 0.1% phenylethylacetylurea (PEAU) when reconstituted in an aqueous solution after storage of the lyophilized Phenobarbital Sodium for up to 6 months at room temperature (RT) and accelerated stability conditions (ACC).

In another embodiment, the lyophilized Phenobarbital Sodium forms no more than 0.05% phenylethylacetylurea (PEAU) when reconstituted in an aqueous solution after storage of the lyophilized Phenobarbital Sodium for up to 6 months at room temperature (RT) and accelerated stability conditions (ACC).

In another embodiment, the lyophilized Phenobarbital Sodium forms no detectable amount of 2-ethyl-2-phenylmalonamide (2EPMM) or alpha-phenylbutyrylguanidine (PBG) when reconstituted in an aqueous solution after storage of the lyophilized Phenobarbital Sodium for up to 6 months at room temperature (RT) and accelerated stability conditions (ACC).

In another embodiment, the lyophilized Phenobarbital Sodium is stable up to at least 6 months at accelerated stability conditions (ACC) which is equivalent to 24 months at room temperature (RT).

In another embodiment, the stability of the lyophilized Phenobarbital Sodium is determined by adding the lyophilized Phenobarbital Sodium to an aqueous solution to form a reconstituted lyophilized Phenobarbital Sodium and analyzing to quantitate the amount of phenylethylacetylurea (PEAU), 2-ethyl-2-phenylmalonamide (2EPMM), and/or alpha-phenylbutyrylguanidine (PBG) in the reconstituted lyophilize Phenobarbital Sodium.

In another embodiment, the Phenobarbital Sodium solution is at a concentration of 65 mg/mL, 100 mg/mL, 130 mg/mL or 200 mg/mL.

In another embodiment, the method further includes filtering the Phenobarbital Sodium solution prior to lyophilizing.

In another embodiment, the method further includes aliquoting the Phenobarbital Sodium solution into a vial prior to lyophilization; and after lyophilization, applying a closure to the vial under vacuum.

Another embodiment is directed to a method of treating an individual in need of Phenobarbital Sodium. The method includes adding saline or dextrose to a composition containing lyophilized amorphous Phenobarbital Sodium immediately prior to administration to form a Phenobarbital Sodium solution; and administering the Phenobarbital Sodium solution to the individual.

In another embodiment, the individual suffers from epilepsy.

In another embodiment, the individual is a newborn suffering from neonatal epilepsy.

In another embodiment, the composition is a powder dose of 65 mg, 100, 130 mg or 200 mg.

In another embodiment, the administering includes intramuscular injection or intravenous injection.

Figure 5B:
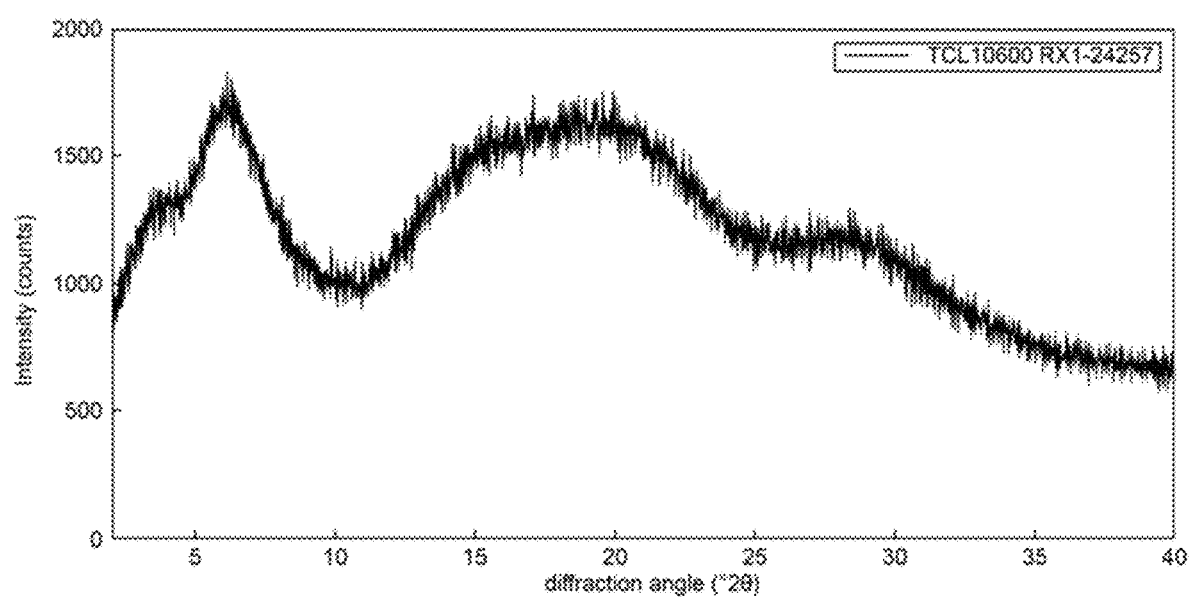
FIG. 5B is an XRPD pattern of Phenobarbital Sodium for Injection, USP, 65 mg/vial.
Figure 5C:
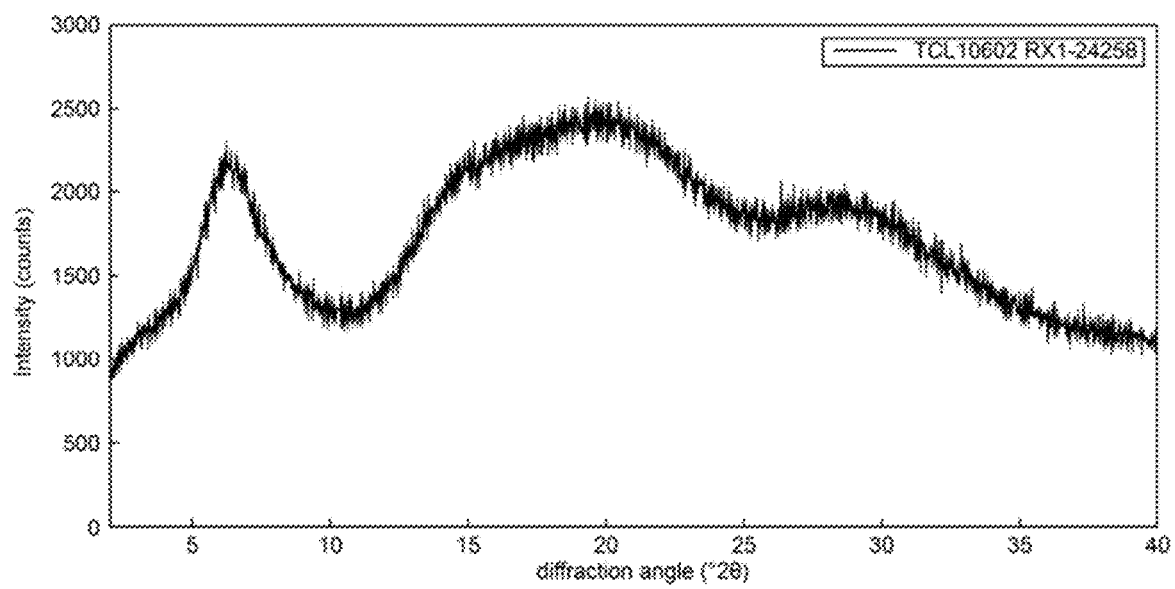
FIG. 5C is an XRPD pattern of Phenobarbital Sodium for Injection, USP, 130 mg/vial.
Figure 5D:
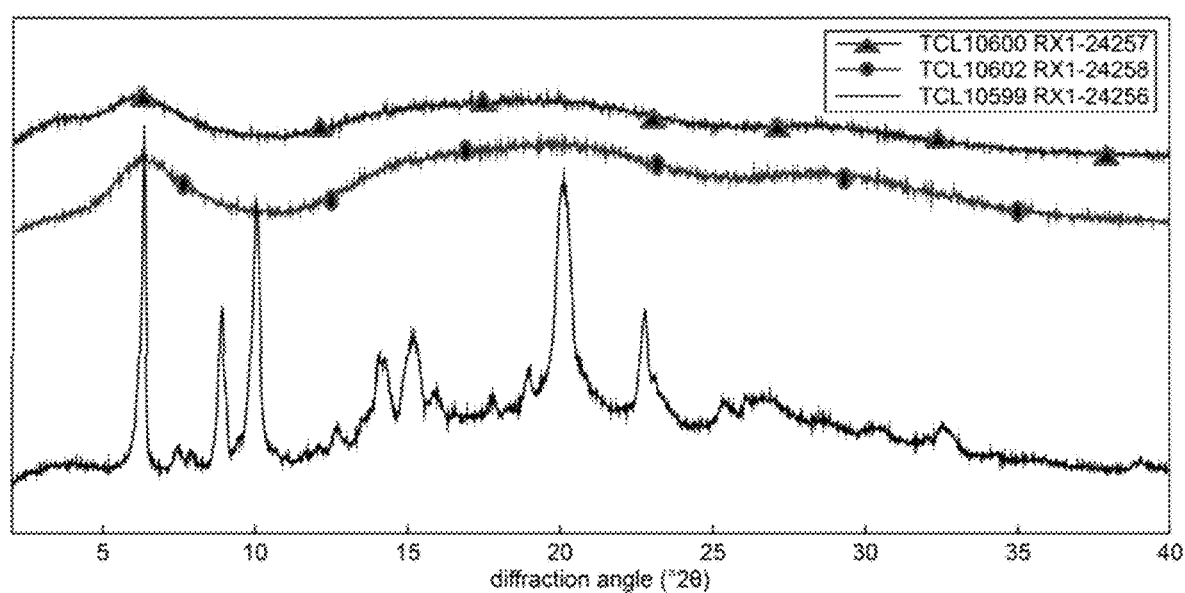
FIG. 5D is a stack plot of the XRPD patterns of FIGS. 5A, 5B, and 5C.

Surprisingly, the inventors have determined that the presently disclosed method produces a storage-stable lyophilized Phenobarbital Sodium that maintains its stability up to at least 6 months under accelerated stability conditions which is equivalent to 24 months at RT. With reference to FIGS. 5B-5C, the lyophilized Phenobarbital Sodium is amorphous. In particular, the lyophilized Phenobarbital Sodium is non-crystalline unlike the USP grade P API shown comparatively in FIG. 5D. The lyophilized Phenobarbital Sodium is stable and ready for reconstitution in either water for injection, 0.9% Saline or 5% Dextrose for intravenous (IV) or intramuscular (IM) administration. The presently disclosed formulation does not contain any organic solvents or preservatives which is specifically advantageous for administration to newborns and neonates. Moreover, the resulting lyophilized Phenobarbital Sodium forms below the quantitation limit of 0.05% phenylethylacetylurea (PEAU), and no detectable amount of 2-ethyl-2-phenylmalonamide (2EPMM) or alpha-phenylbutyrylguanidine (PBG) when reconstituted in water after storage of the lyophilized Phenobarbital Sodium for up to 6 months under accelerated stability conditions which is equivalent to 24 months at RT.

In a comparison analysis, the presently disclosed lyophilized powder of Phenobarbital Sodium at 65 mg or 130 mg doses was reconstituted in water and assayed for impurities and stability along with marketed liquid formulation of Phenobarbital Sodium for Injection USP, 65 mg/mL or 130 mg/mL (Westward Pharmaceuticals). The formulation details for this comparative analysis are presented in Table 1. Representative chromatograms from HPLC analysis are shown in FIGS. 2A-2H, 3A-3L, and 4A-4L.

TABLE 1

Formulation Details

| Dosage form | | Liquid | Lyophilized |
|---|---|---|---|
| Components | Chemical name | mg/mL | mg/vial |
| Drug Substance | Phenobarbital Sodium | 65 or 130 | 65 or 130 |

TABLE 1-continued

Formulation Details

| Dosage form | | Liquid | Lyophilized |
|---|---|---|---|
| Components | Chemical name | mg/mL | mg/vial |
| Inactive ingredients | Propylene Glycol | 705 | NA |
| | Benzyl alcohol | 15.6 | NA |
| | Ethanol | 78.9 | NA |
| | HCL | For pH adjustment | NA |
| | Water for Injection | QS (Quantity Supplied) | NA |

Lyophilized Phenobarbital Sodium for Injection USP, 65 mg/vial and 130 mg/vial
Liquid Phenobarbital Sodium for Injection USP, 65 mg/mL or 130 mg/mL With reference to Tables 2 and 3, the presently disclosed 65 mg lyophilized Phenobarbital Sodium composition was reconstituted in water and compared to the 65 mg Liquid Phenobarbital Sodium for Injection USP (65 mg/mL marketed Liquid Formulation) (Table 2) (FIGS. 3A-3F, FIGS. 4A-4F), and the presently disclosed 130 mg lyophilized Phenobarbital Sodium for Injection USP (130 mg/vial) composition was reconstituted in water and compared to the 130 mg liquid Phenobarbital Sodium for Injection USP (130 mg/mL marketed Liquid Formulation) (Table 3) (FIGS. 3G-3L, FIGS. 4G-4L). In addition to the noted characteristics of each product, the products were assayed for the degradation products—phenylethylacetylurea (PEAU), 2-ethyl-2-phenylmalonamide (2EPMM), and alpha-phenylbutyrylguanidine (PBG) by HPLC analysis, as further described in the Examples. As indicated in both Tables 2 and 3, the initial amount of PEAU (phenylethylacetylurea) assayed in the 65 mg/mL and 130 mg/mL liquid formulations was 0.5% and 0.5%, respectively. Comparatively, no initial amount of PEAU was detected in either the 65 mg or 130 mg lyophilized Phenobarbital Sodium compositions. Furthermore, after 3 and 6 months from the date of manufacture, both the liquid and lyophilized formulations at 65 mg/mL and 130 mg/mL stored at room temperature (RT) (25° C.) and under accelerated stability conditions (ACC) at 40° C. were analyzed by HPLC for assay and related substances. Under these conditions, the amount of PEAU assayed in the 65 mg/mL liquid formulations at 3 months was 1.0% (RT) and 3.7% (ACC) and at 6 months was 1.4% (RT) and 5.8% (ACC) (Table 2). Similarly, the amount of PEAU assayed in 130 mg/mL liquid formulations at 3 months was 0.9% (RT) and 2.8% (ACC) and at 6 months was 1.1% (RT) and 4.3% (ACC) (Table 3). In contrast, for the presently disclosed lyophilized compositions, the amount of PEAU assayed at 3 and 6 months for the 65 mg and the 130 mg lyophilized Phenobarbital Sodium compositions was below quantitation limit (BQL) (0.05%) both at RT and ACC stability conditions (Tables 2-3).

TABLE 2

65 mg/ml Liquid Formulation and 65 mg/vial Lyophilized Powder

Product Name

| Phenobarbital Sodium for Injection USP, 65 mg/mL (Marketed product) | Phenobarbital Sodium for Injection USP, 65 mg/Vial (Nivagen formulation- NPH1907) |
|---|---|

Formulation Type

| Liquid | | | | Lyophilized powder | | | | |
|---|---|---|---|---|---|---|---|---|

Stability Data

| 3 Months | | 6 Months | | 3 Months | | 6 Months | | 15 Months |
|---|---|---|---|---|---|---|---|---|
| RT 25° C., | ACC 40° C., | RT 25° C., | ACC 40° C., | RT 25° C., | ACC 40° C., | RT 25° C., | ACC 40° C., | RT** 25° C., |

TABLE 2-continued 65 mg/ml Liquid Formulation and 65 mg/vial Lyophilized Powder

| Test | Initial | 60% RH | 75% RH | 60% RH | 75% RH | Initial | 60% RH | 75% RH | 60% RH | 75% RH | 60% RH |
|---|---|---|---|---|---|---|---|---|---|---|---|
| Description | CCVS | CCVS | CCVS | CCVS | CCVS | WLP | WLP | WLP | WLP | WLP | WLP |
| Appearance after reconstitution | NA | NA | NA | NA | NA | CCS | CCS | CCS | CCS | CCS | CCS |
| Identification | $ | $ | $ | $ | $ | $ | $ | $ | $ | $ | $ |
| pH* | 9.3 | 9.8 | 9.7 | 9.6 | 9.6 | 9.8 | 9.6 | 9.6 | 9.7 | 9.7 | 9.8 |
| % Assay of Phenobarbital Sodium | 102.4 | 97.6 | 103.1 | 96.3 | 86.7 | 99.1 | 98.7 | 97.4 | 100.0 | 99.3 | 96.0 |
| % degradation (Area percent) 2EPMM | ND | ND | BQL | BQL | BQL | ND | ND | ND | ND | ND | ND |
| PBG | ND | ND | ND | ND | ND | ND | ND | ND | ND | ND | ND |
| PEAU | 0.5 | 1.0 | 3.7 | 1.4 | 5.8 | ND | BQL | BQL | BQL | BQL | BQL |
| Any unspecified degradation product | BQL | BQL | 0.1 | BQL | 0.3 | BQL | BQL | BQL | 0.07 | 0.06 | 0.04 |
| Total degradation products | 0.5 | 1.0 | 3.8 | 1.4 | 6.1 | BQL | BQL | BQL | 0.07 | 0.06 | 0.04 |

CCVS: Clear Colorless Viscous Solution;
CCS: Clear Colorless Solution;
WLP: White Lyophilized powder
$: In Assay analysis, the retention time of Phenobarbital in standard and sample solutions should be same.
BQL: Below Quantitation Limit; (QL-0.05%);
ND: Not Detected
2EPMM: 2-Ethyl-2-Phenylmalonamide, monohydrate;
PBG: α-phenylbutyrylguanidine,
PEAU: phenylethylacetylurea or Pheneturide
*pH of both liquid and lyophilized formulations are measured at 65 mg/mL concentration
**The samples were stored at 30 ± 2° C., 65% RH ± 5

Notably, the Lyophilized powder was stable even after 15 months, and no significant increase in the impurities was observed, rendering such formulation superior to known liquid formulations and enable easy administration.

TABLE 3

130 mg/mL Liquid Formulation and 130 mg/vial Lyophilized formulation

| | Product Name | | | | | | | | | | |
|---|---|---|---|---|---|---|---|---|---|---|---|
| | Phenobarbital Sodium for Injection USP, 130 mg/mL (Marketed product) | | | | | Phenobarbital Sodium for Injection USP, 130 mg/vial (Nivagen formulation-NPH1912) | | | | | |
| | Formulation Type | | | | | | | | | | |
| | Liquid | | | | | Lyophilized powder | | | | | |
| | Stability Data | | | | | | | | | | |
| | | 3 Months | | 6 Months | | | 3 Months | | 6 Months | | 15 Months |
| Test | Initial | RT 25° C., 60% RH | ACC 40° C., 75% RH | RT 25° C., 60% RH | ACC 40° C., 75% RH | Initial | RT 25° C., 60% RH | ACC 40° C., 75% RH | RT 25° C., 60% RH | ACC 40° C., 75% RH | RT** 25° C., 60% RH |
| Description | CCVS | CCVS | CCVS | CCVS | CCVS | WLP | WLP | WLP | WLP | WLP | WLP |
| Appearance after reconstitution | NA | NA | NA | NA | NA | CCS | CCS | CCS | CCS | CCS | CCS |
| Identification | $ | $ | $ | $ | $ | $ | $ | $ | $ | $ | $ |
| pH* | 9.5 | 9.9 | 9.9 | 9.8 | 9.7 | 9.8 | 9.8 | 9.8 | 9.8 | 9.8 | 10.0 |
| % Assay of Phenobarbital Sodium | 100.8 | 95.5 | 92.9 | 95.2 | 90.9 | 98.3 | 100.1 | 97.9 | 100.2 | 99.4 | 98.3 |
| Related Substances (% Area) 2EPMM | ND | ND | BQL | BQL | BQL | ND | ND | ND | ND | ND | ND |

TABLE 3-continued 130 mg/mL Liquid Formulation and 130 mg/vial Lyophilized formulation

| | | | | | | | | | | | |
|---|---|---|---|---|---|---|---|---|---|---|---|
| PBG | ND | ND | ND | ND | ND | ND | ND | ND | ND | ND | ND |
| PEAU | 0.5 | 0.9 | 2.8 | 1.1 | 4.3 | ND | BQL | BQL | BQL | BQL | BQL |
| Any unspecified degradation product | ND | BQL | 0.1 | BQL | 0.4 | BQL | BQL | BQL | 0.05 | 0.05 | 0.04 |
| Total degradation products | 0.5 | 0.9 | 2.9 | 1.1 | 4.7 | BQL | BQL | BQL | 0.05 | 0.05 | 0.04 |

CCVS: Clear Colorless Viscous Solution;
CCS: Clear Colorless Solution;
WLP: White Lyophilized powder
$: In Assay analysis, the retention time of Phenobarbital in standard and sample solutions should be same.
BQL: Below Quantitation Limit; (QL-0.05%);
ND: Not Detected
2EPMM: 2-Ethyl-2-Phenylmalonamide, monohydrate;
PBG: α-phenylbutyrylguanidine,
PEAU: phenylethylacetylurea or Pheneturide
*pH for liquid formulation is measured at 130 mg/mL and for lyophilized formulation at 100 mg/mL dilution
**The samples were stored at 30 ± 2° C., 65% RH ± 5

In typical embodiments, the method of reducing formation of degradation products of a lyophilized Phenobarbital Sodium composition reconstituted in water results in the reconstituted solution having no less than 96% Phenobarbital Sodium. In more typical embodiments, the reconstituted solution has no less than 97% Phenobarbital Sodium. In more preferred embodiments, the reconstituted solution has no less than 98% Phenobarbital Sodium. In additional or alternative embodiments, the reconstituted solution has no quantitative amount (e.g., 0.05% or less) of PEAU, 2 EPMM, or PBG.

According to contemplated embodiments, assaying the stability of the lyophilized Phenobarbital Sodium composition includes reconstituting the composition in water at a concentration of 65 mg/mL, 100 mg/mL, 130 mg/mL or 200 mg/mL.

Further aspects of the present disclosure include methods of treating an individual in need of Phenobarbital Sodium. For administration to an individual (e.g., a human patient) the lyophilized powder of Phenobarbital Sodium powder may be reconstituted in saline or dextrose as disclosed herein immediately prior to administration to form a Phenobarbital Sodium reconstituted solution. In particular embodiments, the individual in need of Phenobarbital Sodium suffers from epilepsy. In preferred embodiments, the individual in need of Phenobarbital Sodium is a newborn suffering from neonatal epilepsy. In other embodiments, the lyophilized Phenobarbital Sodium is a powder dose of 65 mg, 100 mg, 130 mg or 200 mg. In typical embodiments, the administering of the Phenobarbital Sodium reconstituted solution to the individual includes intramuscular injection or intravenous injection.

EXAMPLES

Lyophilization Microscopy. Lyophilization microscopy (FIGS. 1A-1F) was performed using a Leica DM LP microscope equipped with a Linkam FDCS196 stage, TMS93 controller, vacuum pump, LNP unit, and a Spot Insight color camera. A 20×, 040 N.A. objective was used with crossed polarizers and a first order red compensator to view sample. Images were acquired using Spot Advanced software (v.4.5.9).

Lyophilization parameters for the lyophilization microscopy including a start temperature of −50° C. with heating at 1° C./minute to −40° C. followed by heating at 0.5° C./minute to −32.0° C.

HPLC Assays. High Performance Liquid Chromatography (HPLC) was used to assay Phenobarbital Sodium standards and sample solutions as disclosed herein (e.g., Tables 2, 3, FIGS. 3A-3L, and 4A-4L). Both Ultra High-Performance Liquid Chromatographic system (UHPLC) and High-Performance Liquid Chromatographic system (HPLC) (ThermoFisher/Waters) were used together with Data Acquisition Software (Empower 3), equipped with UV and Photodiode Array Detector (UV and PDA), column thermostat and auto sampler compartments or equivalent HPLC system and software.

An exemplary HPLC assay protocol is provided in the following:

Instruments/Apparatus: HPLC with UV detector/PDA Detector, Analytical balance, Sonicator, Volumetric flasks, Beakers, Pipettes.

Reagents, Solvents, Standards: Phenobarbital Reference Standard, Deionized water/Water for Injection, Potassium Monobasic Phosphate, Acetonitrile.

Preparation of Mobile Phase Solutions: Potassium phosphate monobasic (7 mM) and Acetonitrile (70:30) pH 4.5-6.5; Diluent: Mobile phase as a diluent.

Wash Solvent: Water:Acetonitrile (70:30)

CHROMATOGRAPHIC CONDITIONS: The liquid chromatography equipped with a UV and PDA detector, an injector and a data processor is operated as follows:

| Parameters | Conditions |
|---|---|
| Column | L7 packaging column, 150 × 4.6 mm, Particle Size: 5 μm or equivalent |
| Flow rate | 0.9-1.2 mL/min. |
| Detection Wavelength | 254 ± 2 nm for assay and 210 ± 2 nm for Related Substances |
| Injection volume | 10 μL |
| Run time | 15 Minutes |
| Column Oven Temperature | 30° C. |
| Sampler Cooler Temperature | 25° C. |

-continued

| Parameters | Conditions |
|---|---|
| Retention Time | About 5 minutes for Phenobarbital |
| Pump Mode | Isocratic |

Phenobarbital Assay Standard Solution: 0.2 mg/mL to 0.8 mg/mL in diluent; Phenobarbital Related Substances Standard Solution: 0.26 µg/mL to 15.6 µg/mL in diluent; Phenobarbital Related Substances resolution standard solution: 0.475 mg/mL Phenobarbital and about 1 µg/mL for related substances (2-Ethyl-2-Phenyl malonamide, monohydrate (2EPMM), Phenylbutyrylguanidine (PBG) and Phenylethylacetylurea (PEAU) in diluent; Phenobarbital Sodium Sample Solution for Assay: 0.26 mg/mL to 0.78 mg/mL in diluent Phenobarbital Sodium related Substances sample solution: 0.52 mg/mL of Phenobarbital Sodium and related substances 2-Ethyl-2-Phenylmalonamide, monohydrate (2EPMM), Phenyl butyrylguanidine (PBG) and Phenylethylacetylurea (PEAU) and any unspecified degradation products at 0.26 µg/mL to 13.2 µg/mL SYSTEM SUITABILITY REQUIREMENTS: The relative standard deviation of Phenobarbital peak from Six replication injections of related substances standard should not be more than 6.0%. The related standard deviation of Phenobarbital peak from five replicate injections in assay standard solution should not be more than 2.0%. Tailing factor for the Phenobarbital is not more than 2.0. USP Plate count for the Phenobarbital is not less than 2500. The S/N Ratio of the Sensitivity Standard Solution is NLT 10 for related substance test. The resolution between Phenobarbital peak and nearest impurity peak is NLT 1.5

Two alternative formulations are disclosed in Table 6. One of these formulations is 200 mg/vial, Phenobarbital Sodium reconstituted in 10 mL of Water for Injection or 5% Dextrose to obtain a concentration of 20 mg/mL. A second formulation is 200 mg/vial of Phenobarbital Sodium along with 90 mg Sodium Chloride reconstituted in 10 mL of Water for Injection to obtain a concentration of 20 mg/mL Phenobarbital Sodium for Injection and 9 mg/mL or 0.9% Sodium Chloride.

TABLE 6

Phenobarbital Sodium for Injection, USP, 200 mg/vial in 10 mL vial. Formulation Details.

| Ingredients | Manufacturer | NPH2031A (Bulk Solution @ 100 mg/ml Phenobarbital Sodium) Compounding at 2-8° C. | | NPH2031B (Bulk Solution @ 100 mg/mL Phenobarbital Sodium and 45 mg/mL Sodium Chloride) Compounding at 2-8° C. Fill Volume: 2.1 mL | |
|---|---|---|---|---|---|
| | | mg/mL (after reconstitution) | mg/vial | mg/mL (after reconstitution) | mg/vial |
| Phenobarbital Sodium | Siegfried USA, LLC | 20 | 200 | 20 | 200 |
| Sodium Chloride | JT Baker | NA | NA | 9 | 90 |
| DI Water | In house | qs | qs | qs | qs |
| 100% Nitrogen | Airgas | NA | NA | NA | NA |
| 10 mL Tubular Serum Bottle clear | | Wheaton Part#223686 | | | |
| 20 mm Igloo Bromobutyl stopper | | Datwyler | | | |
| Seal 20 mm Filp-Cap, Red | | Wheaton Part# 224203 | | | |

Reconstitution Volume 10 mL; Diluents that can be used are Water for Injection, 0.9% Saline or 5% Dextrose.

These formulations along with the previously disclosed formulations were developed to enable physicians and medical staff at hospitals to easily reconstitute to a desired concentration (e.g., 20 mg/mL) and administer the medicine to patients in need thereof. The reconstituted solution is stable at 2-8° C. for 24 hrs and 3 to 4 hrs when stored at RT (see e.g., Tables 7, 8 and 9).

TABLE 7

Reconstituted Solution Stability of Phenobarbital Sodium for Injection USP, 200 mg/vial (NPH2031A Phenobarbital Sodium @ 200 mg/vial) (Reconstitution in 10 mL Water)

| Test | Spec. | Initial DOA: Jun. 5, 2020 | Reconstituted Solution Stability after 20 hrs DOA: Jun. 6, 2020 | |
|---|---|---|---|---|
| | | | 2-8° C. | RT |
| Description | WLP | WLP | WLP | WLP |
| Appearance | CCS | CCS | CCS | CCS |

TABLE 7-continued

Reconstituted Solution Stability of Phenobarbital Sodium for Injection USP, 200 mg/vial (NPH2031A Phenobarbital Sodium @ 200 mg/vial) (Reconstitution in 10 mL Water)

| Test | Spec. | Initial DOA: Jun. 5, 2020 | Reconstituted Solution Stability after 20 hrs DOA: Jun. 6, 2020 | |
|---|---|---|---|---|
| | | | 2-8° C. | RT |
| pH (20 mg/mL) | 9.2-10.2 | 9.9 | 9.7 | 9.8 |
| % Assay Phenobarbital Sodium | 90.0-105.0 | 100.1 | 100.1 | 100.1 |
| Related Substances (% Area) 2EPMM | NMT 0.2% | BQL | ND | ND |
| PBG | NMT 0.2% | ND | ND | ND |
| PEAU | NMT 0.2% | BQL | 0.03 | 0.03 |
| Any unspecified degradation product | NMT 0.2% | BQL | 0.06 | 0.24 |
| Total degradation products | NMT 1.5% | BQL | 0.09 | 0.27 |
| Water Content by Karl Fischer | NMT 3.0% | 0.84 | NA | NA |
| Note Book Reference | | 192045-163 to 189 | 192045-163-183 | |

DOA: Date of Analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea

TABLE 8

Reconstituted Solution Stability of Phenobarbital Sodium for Injection USP, 200 mg/vial in Sodium Chloride (NPH2031B Phenobarbital Sodium @ 200 mg/vial and Sodium Chloride @ 90 mg/vial) (Reconstitution in 10 mL Water)

| Test | Specification | Initial | Reconstituted Solution Stability after 20 hrs | |
|---|---|---|---|---|
| | | | 2-8° C. | RT |
| Description | WLP | WLP | WLP | WLP |
| Appearance | CCS | CCS | CCS | CCS |
| pH (20 mg/mL) | 9.2-10.2 | 9.8 | 9.7 | 9.8 |
| % Assay Phenobarbital Sodium | 90.0-105.0 | 103.3 | 103.4 | 102.8 |
| Related Substances (% Area) 2EPMM | NMT 0.2% | BQL | ND | BQL |
| PBG | NMT 0.2% | ND | ND | ND |
| PEAU | NMT 0.2% | BQL | 0.03 | 0.03 |
| Any unspecified degradation product | NMT 0.2% | BQL | 0.06 | 0.27 |
| Total degradation products | NMT 1.5% | BQL | 0.09 | 0.3 |
| Water Content by Karl Fischer | NMT 3.0% | 0.84 | NA | NA |

WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea

TABLE 9

Reconstituted Solution Stability of Phenobarbital Sodium for injection USP, 130 mg/vial (NPH2030) (20 mg/mL dilution In Water)

| | | | \multicolumn{7}{c}{Time} | | | | | | |
|---|---|---|---|---|---|---|---|---|
| | | | 2 hrs | | 4 hrs | | 24 hrs | |
| Tests | Shelf life Specifications | Initial | 2-8 C. | RT | 2-8 C. | RT | 2-8 C. | RT |
| Appearance | CCS | CCS | CCS | CCS | CCS | CCS | CCS | CCS |
| pH (20 mg/mL dilution) | 9.2-10.2 | 9.5 | 9.5 | 9.6 | 9.6 | 9.5 | 9.6 | 9.5 |
| Assay of Phenobarbital Sodium | 90.0%-105.0% | 99.8 | 102.1 | 100.8 | 101.7 | 101.2 | 100.4 | 100.3 |
| Related Substances (% Area) 2EPMM | NMT 0.2% | ND | ND | ND | ND | ND | ND | BQL |
| PBG | NMT 0.2% | ND | ND | ND | ND | ND | ND | ND |
| PEAU | NMT 0.2% | BQL | BQL | BQL | BQL | BQL | BQL | BQL |
| Any unspecified degradation product @ RRT 0.37 | NMT 0.2% | 0.015 | 0.02 | 0.04 | 0.02 | 0.06 | 0.04 | 0.18 |
| Total degradation products | NMT 1.5% | 0.015 | 0.02 | 0.04 | 0.02 | 0.06 | 0.04 | 0.18 |
| Osmolality mOsmol/Kg | To be reported | 158 | NP | NP | NP | NP | 159 | 158 |

CCS: Clear colourless solution;
ND: Not detected;
BQL: Below Quantitation limit,
NP: Not performed;
2EPMM: 2-ethylphenylmalonamide monohydrate;
PBG: Phenylbutyrylguanidine;
PEAU: Phenylethylacetylurea Six months stability data for Phenobarbital Sodium for Injection, USP, 65 mg/vial is included in Table 10. Six months stability data for Phenobarbital Sodium for Injection, USP, 130 mg/vial is included in Table 11. Three months stability data for Phenobarbital Sodium for Injection, USP, 200 mg/vial is included in Table 12. Three months stability data for Phenobarbital Sodium for Injection, USP (Phenobarbital Sodium and 9% Saline), 200 mg/vial is included in Table 13.

TABLE 10

| Product Name | Phenobarbital Sodium for Injection USP, 65 mg/vial | Batch#NPH2020 Fill Volume: 1.05 mL | Date Manufactured: Jan. 20, 2020 |
|---|---|---|---|
| Vial Make | 2 mL Fiolax Clear Blow Back Vial (Schott, Article#1590892); | | Date Initiated: Feb. 14, 2020 |
| API Mfg. | Phenobarbital Sodium, USP Grade P, C-IV: Siegfried USA, LLC Lot#1845X007; Re-test Date: Nov. 16, 2023 | | |
| Stopper Used | Aptar stelmi 13 mm Grey Bromobutyl 2 leg Lyophilization Rubber stopper (C1621 6730GC 6 TP3) | | Flip Off Seals: Wheaton, 13 mm Red Plastic top flip off with Aluminum Seal, Lot#224202 |
| Configuration | Inverted | Stability | 25° C., 60% RH (RT) & 40° C., 75% RH (ACC) |

| | | Initial DOA: | 1 Month DOA: Mar. 29, 2020 | | 3 Months DOA: May 20, 2020 | | 6 Months DOA: Sep. 4, 2020 | |
|---|---|---|---|---|---|---|---|---|
| Test | Spec. | Feb. 18, 2020 | RT | ACC | RT | ACC | RT | ACC |
| Description | WLP | WLP | WLP | WLP | WLP | WLP | WLP | WLP |
| Appearance | CCS | CCS | CCS | CCS | CCS | CCS | CCS | CCS |
| pH (65 mg/mL) | 9.2-10.2 | 9.9 | 9.9 | 9.9 | 9.9 | 9.9 | 9.5 | 9.5 |
| % Assay Phenobarbital Sodium | 90.0%-105.0% | 98.6 | 301.6 | 101.5 | 101.3 | 100.5 | 100.0 | 101.2 |

TABLE 10-continued

| | | | | | | | | |
|---|---|---|---|---|---|---|---|---|
| Related Substances (% Area) 2EPMM | NMT 0.2% | BQL | ND | ND | ND | ND | ND | ND |
| PBG | NMT 0.2% | ND | ND | ND | ND | ND | ND | ND |
| PEAU | NMT 0.2% | BQL | BQL | BQL | BQL | BQL | BQL | BQL |
| Any unspecified degradation product | NMT 0.2% | BQL | BQL | BQL | BQL | BQL | BQL | BQL |
| Total degradation products | NMT 1.5% | BQL | BQL | BQL | BQL | BQL | BQL | BQL |
| Water Content by Karl Fischer | NMT 3.0% | 0.6 | 0.9 | 1.3 | 1.4 | 1.5 | 1.5 | 2.1 |
| Note Book Reference | | 192039-150 to 158 | 192046-23 to 45 | | 192045-135 to 153 | | 192051-84 to 122 | |

DOA: Date of Analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea

TABLE 11

| Product Name | Phenobarbital Sodium for Injection USP, 65 mg/vial | Batch#NPH2020 Fill Volume: 1.05 mL | Date Manufactured: Jan. 20, 2020 |
|---|---|---|---|
| Vial Make | 2 mL Fiolax Clear Blow Back Vial (Schott, Article#1590892); | | Date Initiated: Feb. 14, 2020 |
| API Mfg. | Phenobarbital Sodium, USP Grade P, C-IV: Siegfried USA, LLC Lot#1845X007; Re-test Date: Nov. 16, 2023 | | |
| Stopper Used | Aptar stelmi 13 mm Grey Bromobutyl 2 leg Lyophilization Rubber stopper (C1621 6730GC 6 TP3) | | Flip Off Seals: Wheaton, 13 mm Red Plastic top flip off with Aluminum Seal, Lot#224202 |
| Configuration | Inverted | Stability | 25° C., 60% RH (RT) & 40° C., 75% RH (ACC) |

| | | Initial DOA: | 1 Month DOA: Mar. 23, 2020 | | 3 Months DOA: May 20, 2020 | | 6 Months DOA: Sep. 4, 2020 | |
|---|---|---|---|---|---|---|---|---|
| Test | Spec. | Feb. 18, 2020 | RT | ACC | RT | ACC | RT | ACC |
| Description | WLP | WLP | WLP | WLP | WLP | WLP | WLP | WLP |
| Appearance | CCS | CCS | CCS | CCS | CCS | CCS | CCS | CCS |
| pH (65 mg/mL) | 9.2-10.2 | 9.9 | 9.9 | 9.9 | 9.9 | 9.9 | 9.5 | 9.5 |
| % Assay Phenobarbital Sodium | 90.0%-105.0% | 98.6 | 101.6 | 101.5 | 101.3 | 100.5 | 100.0 | 101.2 |
| Related Substances (% Area) 2EPMM | NMT 0.2% | BQL | ND | ND | ND | ND | ND | ND |
| PBG | NMT 0.2% | ND | ND | ND | ND | ND | ND | ND |
| PEAU | NMT 0.2% | BQL | BQL | BQL | BQL | BQL | BQL | BQL |
| Any unspecified degradation product | NMT 0.2% | BQL | BQL | BQL | BQL | BQL | BQL | BQL |
| Total degradation products | NMT 1.5% | BQL | BQL | BQL | BQL | BQL | BQL | BQL |
| Water Content by Karl Fischer | NMT 3.0% | 0.6 | 0.9 | 1.3 | 1.4 | 1.5 | 1.5 | 2.1 |
| Note Book Reference | | 192039-150 to 158 | 192045-23 to 45 | | 192045-135 to 153 | | 192051-84 to 122 | |

DOA: Date of Analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea

TABLE 12

| | | | 3 Months | |
| --- | --- | --- | --- | --- |
| | | Initial DOA: | DOA: Sep. 4, 2020 | |
| Test | Spec. | Jun. 5, 2020 | RT | ACC |
| Description | WLP | WLP | WLP | WLP |
| Appearance | CCS | CCS | CCS | CCS |
| pH (20 mg/mL) | 9.2-10.2 | 9.9 | 9.6 | 9.7 |
| % Assay Phenobarbital Sodium | 90.0-105.0 | 100.1 | 98.1 | 101.0 |
| Related Substances (% Area) 2EPMM | NMT 0.2% | ND | ND | ND |
| PBG | NMT 0.2% | ND | ND | ND |
| PEAU | NMT 0.2% | BQL | 0.03 | 0.04 |
| Any unspecified degradation product | NMT 0.2% | BQL | 0.06 | 0.05 |
| Total degradation products | NMT 1.5% | BQL | 0.09 | 0.09 |
| Water Content by Karl Fischer | NMT 3.0% | 1.1 | 1.0 | 1.3 |
| Note Book Reference | | 192045-163 to 189 | 192051-84 to 122 | |

Product Name: Phenobarbital Sodium for Injection USP, 200 mg/vial
Vial Make: 10 mL Tubular Serum Bottle Clear Wheaton, Part# 223586; Batch#5192875);
API Mfg.: Phenobarbital Sodium, USP Grade P, C-IV: Siegfried USA, LLC Lot#1924X009; Re-test Date: Jul. 20, 2024
Stopper Used: Datwyler 20 mm Igloo Bromobutyl Lyophilization Rubber stopper
Batch#NPH2031A
Fill Volume: 2.1 mL
Flip Off Seals: Wheaton, 20 mm Red Plastic top flip off with Aluminum Seal, Lot#224203
Configuration: Inverted
Stability: 25° C., 60% RH (RT) & 40° C., 75% RH (ACC)
Date Manufactured: Jun. 3, 2020
Date Initiated: Jun. 9, 2020

DOA: Date of Analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea

TABLE 13

Product Name: Phenobarbital Sodium for Injection USP, 200 mg/vial
Vial Make: 10 mL Tubular Serum Bottle Clear Wheaton, Part# 223586; Batch#5192875);
API Mfg.: Phenobarbital Sodium, USP Grade P, C-IV: Siegfried USA, LLC Lot#1924X009; Re-test Date: Jul. 20, 2024
Stopper Used: Datwyler 20 mm Igloo Bromobutyl Lyophilization Rubber stopper
Batch#NPH2031A
Fill Volume: 2.1 mL
Flip Off Seals: Wheaton, 20 mm Red Plastic top flip off with Aluminum Seal, Lot#224203
Configuration: Inverted
Stability: 25° C., 60% RH (RT) & 40° C., 75% RH (ACC)
Date Manufactured: Jun. 3, 2020
Date Initiated: Jun. 9, 2020

| | | | 3 Months | |
| --- | --- | --- | --- | --- |
| | | Initial DOA: | DOA: Sep. 4, 2020 | |
| Test | Spec. | Jun. 5, 2020 | RT | ACC |
| Description | WLP | WLP | WLP | WLP |
| Appearance | CCS | CCS | CCS | CCS |
| pH (20 mg/mL) | 9.2-10.2 | 9.8 | 9.5 | 9.5 |
| % Assay Phenobarbital Sodium | 90.0-105.0 | 103.3 | 102.8 | 103.6 |
| Related Substances | NMT 0.2% | BQL | ND | ND |

TABLE 13-continued

| (% Area) | | | | |
|---|---|---|---|---|
| 2EPMM | | | | |
| PBG | NMT 0.2% | ND | ND | ND |
| PEAU | NMT 0.2% | BQL | 0.03 | 0.04 |
| Any unspecified degradation product | NMT 0.2% | BQL | 0.06 | 0.05 |
| Total degradation products | NMT 1.5% | BQL | 0.1 | 0.08 |
| Water Content by Karl Fischer | NMT 3.0% | 0.8 | 0.9 | 1.1 |
| Note Book Reference | | 192045-163 to 189 | 192051-84 to 122 | |

DOA: Date of Analysis;
WLP: White Lyophilized Powder;
CCS: Clear Colorless Solution, 1 minute after reconstitution;
ND: Not Detected;
NMT: Not More Than;
BQL: Below Quantitation Limit (0.05%)
2EPMM: 2-Ethyl-2-Phenylmalonamide, monohydrate;
PBG: α-Phenylbutyrylguanidine;
PEAU: Phenylethylacetylurea Data for Osmolality, Particulate matter and assay for Sodium Chloride is disclosed in Table 14.

TABLE 14

Phenobarbital Sodium for Injection, USP, 200 mg/vial in Water or Sodium Chloride - Osmolality, Particulate Matter and Assay for Sodium Chloride.

| Batch No | Osmolality* (mOsmol/Kg) (Specification: To be reported) Reconstitution in 10 mL (20 mg/mL) | Particulate Matter (By Light Obscuration method) Ref: USP<788> | | Assay of Sodium Chloride (titrimetric; Ref USP monograph for Sodium Chloride Injection Specification: (95.0%-105.0%) |
|---|---|---|---|---|
| | | ≥10 μM Specification: (NMT 6000 particles/vial) | ≥25 μM Specification: (NMT 600 particles/vial | |
| NPH2031A (200 mg/vial) | 148 | 80.0 | 0.67 | NA |
| NPH2031B (200 mg/vial) (Phenobarbital Sodium 200 mg, 9% Sodium Chloride) | 372 | 171 | 1.33 | 99.99 |
| Water-Blank | 0 | NA | NA | NA |
| 0.9% Sodium Chloride | 270 | NA | NA | NA |

Lyophilization parameters used for the 65 mg/vial, 100 mg/vial, 130 mg/vial and 200 mg/vial are disclosed in Table 15.

TABLE 15

Lyophilization Cycle parameters.

| Section | Phase | Lyophilization Cycle 1* | | | | Lyophilization Cycle 2** | | | |
|---|---|---|---|---|---|---|---|---|---|
| | | Condenser set point ° C. | Vacuum [mTorr] | Temperature ° C. | Hold Time [mm] | Condenser set point ° C. | Vacuum [mTorr] | Temperature ° C. | Hold Time [mm] |
| 1 | Loading | | off | 5 | n.a. | | off | −5 | n.a. |
| 2 | Freezing | | off | −5 | 5 | | off | −5 | 10 |
| 3 | Freezing | | off | −50 | 60 | | off | −52 | 120 (Ramp) |

TABLE 15-continued

Lyophilization Cycle parameters.

| | | Lyophilization Cycle 1* | | | | Lyophilization Cycle 2** | | | |
|---|---|---|---|---|---|---|---|---|---|
| Section | Phase | Condenser set point °C. | Vacuum [mTorr] | Temperature °C. | Hold Time [mm] | Condenser set point °C. | Vacuum [mTorr] | Temperature °C. | Hold Time [mm] |
| 4 | Freezing | | off | −10 | 30 | | off | −52 | 180 (Hold) |
| 5 | Freezing | | off | −50 | 120 | | n.a. | n.a. | n.a. |
| 6 | Evacuation | −50 | 75 | −50 | 30 | −60 | 50 | −45 | 30 |
| 7 | Primary drying | | 75 | −50 | 400 (Hold) | | 50 | −42 | 100 (Ramp) |
| 8 | Primary drying | | 75 | −45 | 350 (Hold) | | 50 | −42 | 1120 (Hold) |
| 9 | Primary drying | | 75 | −43 | 300 (Hold) | | n.a. | n.a. | n.a. |
| 10 | Primary drying | | 75 | −35 | 250 (Hold) | | n.a. | n.a. | n.a. |
| 11 | Primary drying | | 75 | −20 | 60 (Hold) | | n.a. | n.a. | n.a. |
| 12 | Primary drying | | 75 | 0 | 120 (Hold) | | n.a. | n.a. | n.a. |
| 13 | secondary drying | | 75 | 50 | 120 (Hold) | | 50 | 35 | 100 (Ramp) |
| 14 | secondary drying | | 75 | 25 | 120 (Hold) | | 50 | 35 | 420 (Hold) |

Lyophilization Cycle 1*: 65 mg/vial, 130 mg/vial and 100 mg/vial samples disclosed in Tables 1, 2, 3, 16 and 17
Lyophilization Cycle 2**: NPH2031A (200 mg/vial Phenobarbital Sodium) and NPH2031B (200 mg/vial in Phenobarbital Sodium and 90 mg/vial Sodium Chloride, NPH2020 (65 mg/vial) and NPH2021 (130 mg/vial)

Six months stability data for Phenobarbital Sodium for Injection USP, 100 mg/vial is included in Table 16.

TABLE 16

| Product Name | Phenobarbital Sodium for Injection USP, 100 mg/vial | Batch#NPH1980 | Date Manufactured: Sep. 25, 2019 |
|---|---|---|---|
| Vial Make | 5 mL Clear Untreated Article#9621139054 5 mL Clear Treated Article#9621130486 | | Date Initiated: Sep. 30, 2019 |
| API Mfg. | Phenobarbital Sodium, USP Grade P, C-IV: Siegfried USA, LLC Lot#1845X006; Re-test Date: Nov. 16, 2023 | | |
| Stopper Used | Aptar stelmi 13 mm Grey Bromobutyl 2 leg Lyophilization Rubber stopper, Lot#G702/91884 | | Flip Off Seals: Wheaton, 13 mm Red Plastic top flip off with Aluminum Seal, Lot# NA |
| Configuration | Inverted | Stability | 25° C., 60% RH (RT) & 40° C., 75% RH (ACC) |

| | | Initial | | 1 Month | | | | 3 Months | | | | 6 Months | | | |
|---|---|---|---|---|---|---|---|---|---|---|---|---|---|---|---|
| | | | | RT | | ACC | | RT | | ACC | | RT | | ACC | |
| Test | Spec. | UT | T | UT | T | UT | T | UT | T | UT | T | UT | T | UT | T |
| Description | WLP | WLP | WLP | WLP | WLP | WLP | WLP | WLP | WLP | WLP | WLP | WLP | WLP | WLP | WLP |
| Appearance | CCS | CCS | CCS | CCS | CCS | CCS | CCS | CCS | CCS | CCS | CCS | CCS | CCS | CCS | CCS |
| pH | 9.2–10.2 | 9.7 | 9.7 | 9.6 | 9.7 | 9.6 | 9.5 | 9.7 | 9.7 | 9.7 | 9.7 | 9.8 | 9.9 | 9.8 | 9.9 |
| % Assay Phenobarbital Sodium | 90.0%–105.0% | 98.4 | 97.8 | 98.6 | 99.0 | 98.0 | 100.4 | 99.1 | 98.7 | 97.0 | 96.9 | 97.7 | 98.3 | 97.2 | 97.6 |
| Related Substances (% Area) 2EPMM | NMT 0.2% | ND | ND | ND | ND | ND | ND | BQL | BQL | BQL | BQL | ND | ND | ND | ND |
| PBG | NMT 0.2% | ND | ND | ND | ND | ND | ND | ND | ND | ND | ND | ND | ND | ND | ND |
| PEAU | NMT 0.2% | BQL | BQL | BQL | BQL | BQL | BQL | BQL | BQL | BQL | BQL | BQL | BQL | BQL | BQL |
| Any unspecified degradation product | NMT 0.2% | 0.05 | 0.06 | 0.05 | 0.05 | 0.05 | 0.05 | BQL | BQL | BQL | BQL | BQL | BQL | BQL | BQL |
| Total degradation products | NMT 1.5% | 0.06 | 0.06 | 0.05 | 0.05 | 0.05 | 0.05 | BQL | BQL | BQL | BQL | BQL | BQL | BQL | BQL |

TABLE 16-continued

| Water Content by Karl Fischer | NMT 3.0% | 0.7 | 0.6 | 1.0 | 1.0 | 1.1 | 1.3 | 1.2 | 1.1 | 1.6 | 1.5 | 1.6 | 1.2 | 1.5 | 2.0 |
|---|---|---|---|---|---|---|---|---|---|---|---|---|---|---|---|
| Note Book Reference | | 192031-91 to 101 | | | 192031-169 to 183 | | | 192039-44 to 52 | | | 192045-52 to 85 | | | | |

WLP: White Lyophilized powder;
CCS: Clear Colorless Solution, 1 minute after reconstitution;
UT: Untreated;
T: Treated
ND: Not Detected;
NMT: Not More Than;
2EPMM: 2-Ethyl-2-Phenylmalonamide, monohydrate;
PBG: α-Phenylbutyrylguanidine;

TABLE 17

Phenobarbital Sodium for Injection, USP, 100 mg/vial Formulation Details.

| Ingredients | Manufacturer/Lot number | Concentration (mg/mL) | Concentration (mg/vial) | Batch Quantity (100 mL) |
|---|---|---|---|---|
| Phenobarbital Sodium, USP Grade P C-IV | Siegfried USA, LLC Mat No: 300040 Lot# 1845X006 Retest date: Nov. 16, 2023 | 101.13 mg (~100 mg Phenobarbital Sodium after LOD correction) | 100 mg | 10.113 g |
| Water for Injection | In house | Q.S. to 1 mL | NA | Q.S. to 100 mL or 103.3 g |
| 100% Nitrogen | Airgas | NA | NA | NA |
| 5 mL, untreated | Gerresheimer Article#9621139054 | NA | NA | NA |
| 5 mL, treated | Gerresheimer Article#9621130486 | NA | NA | NA |
| 13 mm Bromobutyl Lyophilization stoppers | Aptar-Stelmi C16216720GC6TP3 | NA | NA | NA |
| Seal: 13 mm Seal, Flip-Cap, Red | Wheaton Unlined | NA | NA | NA |

Diluents that can be used: Water for Injection, 0.9% Saline or 5% Dextrose
Proposed Reconstitution Volume: 5 mL Representative chromatograms and/or corresponding calculations are shown in FIGS. 2A-2I1, 3A-3L, 4A-4L, and Tables 2 and 3.

X-Ray Powder Diffraction. With reference to FIGS. 5A-5D, XRPD was performed using the Rigaku Smart-Lab X-ray diffraction system configured for reflection Bragg-Brentano geometry using a line source X-ray beam. The x-ray source is a Cu Long Fine Focus tube that was operated at 40 kV and 44 mA. That source provides an incident beam profile at the sample that changes from a narrow line at high angles to a broad rectangle at low angles. Beam conditioning slits were used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam is controlled by 5.0-degree Soller slits in both the incident and diffracted beam paths. The samples were placed in a low-background, silicon holder using light manual pressure to keep the sample surfaces flat and level with the reference surface of the holder. The samples were analyzed from 2 to 40° 2θ using a continuous scan of 6° 2θ per minute with an effective step size of 0.02° 2θ.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of producing a storage-stable form of lyophilized amorphous phenobarbital sodium composition, comprising:
adding phenobarbital sodium to water to form a phenobarbital sodium solution having a pH of between 9.2 and 10.2, wherein the phenobarbital sodium solution does not contain an organic solvent, and wherein the phenobarbital sodium solution optionally further comprises sodium chloride;
lyophilizing the phenobarbital sodium solution in a container under a protocol comprising a freezing step, a primary drying step, and a secondary drying step to thereby produce the lyophilized amorphous phenobarbital sodium composition;
wherein the freezing step comprises freezing the lyophilized amorphous phenobarbital sodium to a temperature of about −50° C. without application of vacuum;
wherein the primary drying step comprises application of vacuum at a pressure of between about 50 mTorr and 75 mTorr at a temperature of between about −50° C. and about 0° C. for at duration of at least 1,000 minutes;
wherein the secondary drying step comprises application of vacuum at a pressure of between about 50 mTorr and 75 mTorr at a temperature of between about 25° C. and about 50° C. for at duration of at least 200 minutes;
wherein the lyophilized amorphous phenobarbital sodium has an initial moisture content of equal or less than 1.5%; and
wherein the lyophilized amorphous phenobarbital sodium forms, upon storage over 3 months, no more than 0.2% phenylethylacetylurea (PEAU) when reconstituted in an aqueous solution.

2. The method of claim 1, wherein the sodium chloride is present in the phenobarbital sodium solution in an amount that, upon reconstitution of the lyophilized amorphous phenobarbital sodium in the aqueous solution, yields a sodium chloride concentration of 0.9% in the reconstituted solution.

3. The method of claim 1, wherein the phenobarbital sodium solution in the container is present in an amount of about 65 mg, or about 100 mg, or about 130 mg, or about 200 mg.

4. The method of claim 1, wherein the water is sparged with nitrogen.

5. The method of claim 1, wherein the phenobarbital sodium solution does not contain a preservative.

6. The method of claim 1, wherein the primary drying step is performed using at increasing temperatures that increase from about −50° C. to about 0° C. when the amount of phenobarbital sodium in the container is between 65 mg and 130 mg.

7. The method of claim 1, wherein the primary drying step is performed using at constant temperature of about −42° C. when the amount of phenobarbital sodium in the container is 200 mg.

8. The method of claim 1, wherein the secondary drying step is performed using at decreasing temperatures that decrease from about 50° C. to about 25° C. when the amount of phenobarbital sodium in the container is between 65 mg and 130 mg.

9. The method of claim 1, wherein the secondary drying step is performed using at constant temperature of about 35° C. when the amount of phenobarbital sodium in the container is 200 mg.

10. The method of claim 1, wherein the lyophilized amorphous phenobarbital sodium has an initial moisture content of equal or less than 1.2%.

11. The method of claim 1, wherein the lyophilized amorphous phenobarbital sodium has an initial moisture content of equal or less than 1.0%.

12. The method of claim 1, wherein the lyophilized amorphous phenobarbital sodium forms, upon storage over 3 months, no more than 0.1% phenylethylacetylurea (PEAU) when reconstituted in an aqueous solution.

13. The method of claim 1, wherein the lyophilized amorphous phenobarbital sodium forms, upon storage over 3 months, no detectable quantities of 2-ethyl-2-phenylmalonamide (2EPMM) or alpha-phenylbutyrylguanidine (PBG) when reconstituted in an aqueous solution.

14. The method of claim 1, wherein the storage is at 40° C. and 75% relative humidity.

15. The method of claim 1, wherein the lyophilized amorphous phenobarbital sodium composition contains at least 98% lyophilized amorphous phenobarbital sodium.

* * * * *